(12) United States Patent
Popat

(10) Patent No.: US 7,941,245 B1
(45) Date of Patent: May 10, 2011

(54) STATE-BASED SYSTEM FOR AUTOMATED SHADING

(76) Inventor: Pradeep Pranjivan Popat, Arlington, VA (US)

( * ) Notice: Subject to any disclaimer, the term of this patent is extended or adjusted under 35 U.S.C. 154(b) by 89 days.

(21) Appl. No.: 12/153,425

(22) Filed: May 19, 2008

Related U.S. Application Data

(60) Provisional application No. 60/924,613, filed on May 22, 2007.

(51) Int. Cl.
*G01M 1/38* (2006.01)
*E04H 15/48* (2006.01)
*H01H 3/16* (2006.01)
*G08B 13/08* (2006.01)

(52) U.S. Cl. ............ 700/275; 135/155; 200/61.84; 340/545.8; 340/545.9

(58) Field of Classification Search .......... 700/275; 135/155; 200/61.84; 340/545.8, 545.9
See application file for complete search history.

(56) References Cited

U.S. PATENT DOCUMENTS

| | | | |
|---|---|---|---|
| 595,343 A | 12/1897 | Roth | |
| 2,083,726 A | 6/1937 | Mason | |
| 2,149,481 A | 3/1939 | Bosch et al. | |
| 3,204,690 A | 9/1965 | Nye | |
| 3,249,148 A | 5/1966 | Zablodil et al. | |
| 3,294,152 A | 12/1966 | Kuijvenhoven | |
| 3,646,985 A | 3/1972 | Klann | |
| 3,675,023 A | 7/1972 | Kunke et al. | |
| 3,860,055 A | 1/1975 | Wild | |
| 4,096,903 A | 6/1978 | Ringle, III | |
| 4,255,899 A | 3/1981 | Braithwaite | |
| 4,396,831 A | 8/1983 | Yamada et al. | |
| 4,622,470 A | 11/1986 | Makino et al. | |
| 4,644,990 A | 2/1987 | Webb, Sr. et al. | |
| 5,142,133 A | 8/1992 | Kern et al. | |
| 5,237,168 A | 8/1993 | Giust et al. | |
| 5,237,169 A | 8/1993 | Grehant | |
| 5,275,219 A | 1/1994 | Giacomel | |
| 5,347,446 A * | 9/1994 | Iino et al. ................ | 700/29 |
| 5,391,967 A | 2/1995 | Domel et al. | |
| 5,444,339 A | 8/1995 | Domel et al. | |
| 5,495,153 A | 2/1996 | Domel et al. | |
| 5,510,975 A | 4/1996 | Ziegler, Jr. | |
| 5,532,560 A | 7/1996 | Element et al. | |
| 5,598,000 A | 1/1997 | Popat | |
| 5,663,621 A | 9/1997 | Popat | |
| 5,675,487 A * | 10/1997 | Patterson et al. ........ | 700/56 |

(Continued)

OTHER PUBLICATIONS

Reinharr-C., "Lightswitch-2002: A Model for Manual and Automated Control of Electric Lighting and Blinds", 2004, Elsevier, p. 1-14.*

*Primary Examiner* — Albert Decady
*Assistant Examiner* — Thomas Stevens

(57) ABSTRACT

An automated shading system defines an environmental state as a discrete variable representing a history of values of a second discrete variable representing the ambient environment. The system executes a state-specific automated shading command upon occurrence of each state. Prior to usage, each automated shading command is initialized to one of two types of command, as a function of the corresponding state: an "adjust shading" command that causes an automatic adjustment to a predetermined shading setting, or a "do not adjust" command that causes no shading adjustment. The system also enables a user to directly adjust the shading to a selected setting via deliberate shading commands. After each deliberate shading adjustment, the system updates the automated shading command associated with the current state to an "adjust shading" command that, upon subsequent occurrence of the same state, will cause an automatic adjustment to the same selected setting.

6 Claims, 9 Drawing Sheets

U.S. PATENT DOCUMENTS

| | | |
|---|---|---|
| 5,698,958 A | 12/1997 | Domel et al. |
| 5,760,558 A | 6/1998 | Popat |
| 5,907,227 A | 5/1999 | Domel et al. |
| 6,060,852 A | 5/2000 | Domel et al. |
| 6,064,949 A | 5/2000 | Werner et al. |
| 6,066,843 A | 5/2000 | Scheremeta |
| 6,084,231 A | 7/2000 | Popat |
| 6,181,089 B1 | 1/2001 | Kovach et al. |
| 6,201,364 B1 | 3/2001 | Will et al. |
| 6,259,218 B1 | 7/2001 | Kovach et al. |
| 6,298,273 B1 | 10/2001 | Grehant et al. |
| 6,299,115 B1 | 10/2001 | Kovach et al. |
| 6,369,530 B2 | 4/2002 | Kovach et al. |
| 6,484,069 B2 | 11/2002 | Osinga |
| 6,688,368 B2 | 2/2004 | Kovach et al. |
| 6,850,017 B1 | 2/2005 | Domel et al. |
| 6,867,565 B2 | 3/2005 | Maistre et al. |
| 6,912,429 B1 | 6/2005 | Bilger |
| 7,085,627 B2 | 8/2006 | Bamberger et al. |
| 7,107,126 B2 * | 9/2006 | Maistre et al. ............. 700/275 |
| 7,111,952 B2 | 9/2006 | Veskovic |
| 7,155,296 B2 | 12/2006 | Klasson et al. |
| 7,190,139 B2 | 3/2007 | Mommaerts |
| 7,389,806 B2 | 6/2008 | Kates |
| 2005/0015122 A1 * | 1/2005 | Mott et al. ............. 607/88 |
| 2005/0046584 A1 * | 3/2005 | Breed ............. 340/825.72 |

* cited by examiner

30
INITIALIZE SET {commands(j):} TO DEFAULT VALUES

31
DETECT AND RESPOND TO CHANGES IN VALUE OF VARIABLE *state*

32
DETECT AND RESPOND TO *DELIBERATE SHADING COMMANDS*

STATE-BASED SYSTEM FOR AUTOMATED SHADING

CROSS-REFERENCE TO RELATED APPLICATIONS

This application claims the benefit of Provisional Patent Application No. 60/924,613, filed 22 May, 2007, entitled "State-Based System and Method for Automated Window Shading".

BACKGROUND

1. Field of the Invention

This invention relates to automated window shading systems, specifically systems having the object of automatically anticipating a user's shading preferences under changing conditions, and of automatically adjusting the shading according to those preferences.

2. Discussion of Prior Art

Automated Shading Systems

In this disclosure, I use the term inconvenience to refer to the sensory, cognitive, and physical efforts associated with human tasks. Because inconvenience has an important and special meaning in the context of my invention, I use italicized text to refer to it throughout this disclosure (as well as to other terms and phrases with special meanings in the context of my invention).

There is great demand for systems directed toward reducing inconvenience. For purposes of this disclosure, I make a distinction between two types of such system: mechanized systems and automated systems.

Mechanized systems reduce just the physical effort associated with a given task.

Automated systems reduce the cognitive and sensory efforts, as well as the physical effort, associated with a given task.

An important class of automated system is one that attempts to anticipate or emulate human behavior. For example, an object of an automated window-shading system is to anticipate a user's shading preferences under changing conditions, and to automatically adjust the shading according to those preferences—thus sparing the user the cognitive and sensory (as well as physical) efforts associated with making deliberate shading adjustments.

Of course, no automated shading system can fully anticipate the desires of its user, so occasional deliberate shading adjustments will still be necessary. One metric of the effectiveness of such a system is the degree to which it reduces the frequency of required deliberate adjustments. Another important consideration is the effort required to "teach" the system the user's preferences so that it "knows" when and how to adjust the shading.

Thus, an ideal automated shading device would be one that (1) substantially reduces the frequency of required deliberate shading adjustments, and (2) is simple and easy to "teach". Another way of stating this object is that an ideal automated shading device should virtually eliminate the inconvenience associated with window shading—both the short-term inconvenience associated with teaching or programming the system, as well as the long-term inconvenience associated with the need to make deliberate shading adjustments.

Unfortunately, conventional automated shading technology falls far short of this ideal, and instead forces a trade-off between short-term inconvenience and long-term inconvenience:

My research shows that conventional automated shading devices that do not require a complex, inconvenient teaching process (and thereby minimize short-term inconvenience) do not substantially reduce long-term inconvenience.

Conversely, conventional automated shading devices that do reduce long-term inconvenience typically require a complex and inconvenient teaching process, thus resulting in significant short-term inconvenience. Moreover, such systems do not reduce long-term inconvenience enough to justify their purchase by mainstream buyers.

FIG. 1: Inconvenience Associated with Conventional Mechanized Shading Devices

A useful reference point for assessing the inconvenience associated with use of various automated shading devices is the inconvenience associated with use of a mechanized (but non-automated) shading device. Such a device typically uses an electric motor to actuate an adjustable window covering, thereby eliminating much of the physical effort associated with shading adjustments. However, the user must still deliberately initiate every shading adjustment (typically via a remote control), which requires some cognitive, sensory, and physical effort. I use this level of effort as the reference level in discussing the requirements for, and effectiveness of, various automated shading devices.

FIG. 1 is a plot of the relative inconvenience versus time associated with the use of a conventional mechanized shading device. The relative inconvenience is a function of the average frequency of required deliberate adjustments, which in turn depends on factors such as climate and user preferences. However, for the purposes of this discussion, this average frequency may be considered effectively constant. Thus, as shown, the inconvenience is also constant with time, and represents the reference level of inconvenience for purposes of this disclosure.

Categorization of Prior-Art Automated Shading Systems

Conventional automated shading systems can be broadly grouped into three categories:

Sensor-based discrete-control systems automatically adjust the shading to discrete, predetermined settings under predetermined conditions.

Sensor-based continuous-control systems automatically adjust the shading across a continuum of settings as a function of at least one sensed variable.

Clock-based systems automatically adjust the shading to predetermined settings at predetermined times.

Sensor-Based Discrete-Control Systems

A sensor-based discrete-control system adjusts the shading to predetermined settings as a function of the prevailing environmental condition. The environmental condition is a discrete variable representing a combination of one or more discrete variables, each of which has a value that depends on the output of a sensor (e.g., a photocell) relative to one or more predetermined thresholds.

Simple Sensor-Based Discrete Control Systems

For example, a simple system might have a single sensor (e.g., an outward-facing photocell) and use a single threshold (e.g., a threshold representing the brightness at dusk or dawn) to determine the value of a single discrete, binary variable (e.g., representing daytime/nighttime). In such a system, the discrete environmental condition variable has only two possible values (e.g., "daytime" or "nighttime"), and there are only two corresponding predetermined shading settings. When the sensor output crosses the threshold, the shading is automatically adjusted to the setting corresponding to the new environmental condition.

An early example of such a single-sensor system is the automatic shade disclosed in U.S. Pat. No. 2,149,481 to Bosch et al (1939). Bosch et al disclose an embodiment responsive to temperature (as sensed by a thermostat), as well as an embodiment responsive to light level (as sensed by a photocell).

FIG. 2: Inconvenience Associated with Simple Sensor-Based Discrete Control System FIG. 2 shows a plot of estimated inconvenience versus time for a simple sensor-based discrete-control automated shading system capable of only dusk/dawn operation, as described above.

Before use, such systems must be taught, or programmed with, the desired dusk and dawn settings. As shown in FIG. 2, this programming step represents only slightly greater inconvenience than the reference level, and can be completed quickly. However, after programming, such systems do not significantly reduce the inconvenience below the reference level. This is because people generally do not make shading adjustments on the basis of just a single environmental variable (e.g., brightness), so such systems are incapable of effectively anticipating human shading preferences under changing conditions.

Thus, while such systems do not cause excessive short-term inconvenience, neither do they significantly reduce the long-term inconvenience associated with shading adjustments.

Complex Sensor-Based Discrete-Control Systems

Also known in the art are sensor-based discrete-control systems with multiple sensors. Such a system might include, for example, an outward-sensing photocell and an inward-facing Passive InfraRed (PIR) occupancy sensor. These sensor outputs would be compared to appropriate thresholds to obtain the values of a daytime/nighttime binary variable and an occupied/unoccupied binary variable, respectively. These two binary variables, in turn, would define four unique environmental conditions, each of which would be associated with a predetermined shading setting. Such a system would automatically adjust the shading to the corresponding predetermined setting when the output of either sensor crosses the corresponding threshold. Examples of multiple-sensor systems include:

The system disclosed in U.S. Pat. No. 3,675,023 to Kunke et al. (1972). This system includes a light sensor and a heat sensor, with associated control elements, to control the operation of a motorized Venetian blind. The system automatically closes the blind when the outputs of either the light sensor or heat sensor exceed predetermined thresholds, and automatically opens the blind when the outputs of both the light sensor and heat sensor are below predetermined thresholds.

The IntelliFlex® motorized-shade control system with optional Sun-Sensor, manufactured by Draper, Inc. of Spiceland, Ind., which includes optional sun and wind sensors.

FIG. 3: Inconvenience Associated with Complex Sensor-Based Discrete Control System FIG. 3 shows a plot of estimated inconvenience versus time for a sensor-based discrete-control automated shading system using both dusk/dawn and occupancy sensors.

Some such multi-sensor systems are, indeed, capable of providing a noticeable (but still modest) reduction in the frequency of required deliberate shading adjustments and, thus, in long-term inconvenience. However, because these systems recognize a relatively large number of discrete environmental conditions, they must be taught a correspondingly large number of predetermined shading settings, causing substantial short-term inconvenience. This may be an unacceptable trade-off for some users.

Sensor-Based Continuous Control Systems

A sensor-based continuous control system automatically adjusts the shading across a continuous range of settings, in response to the output of one or more sensors, to maintain a desired condition (e.g., a desired interior brightness level). Such systems can be either open-loop or closed-loop:

In an open-loop system, the sensed variable is not affected by the shading setting. For example, an open-loop daylight-control system might sense the daylight level outside a building, and then adjust the shading to maintain a near-constant estimated (versus measured) level of daylight inside the building.

An example of such an open-loop system is the photosensitive automatic blind controller disclosed in U.S. Pat. No. 5,532,560 to Element et al (1996). This system includes an outward facing light sensor, mounted on the outward-facing side of a motorized Venetian blind, to sense the daylight level incident on the blind. The controller automatically adjusts the blind to provide a degree of shading that depends on the output of the light sensor (as well as a user-generated reference level). Note that Element at al use non-standard definitions of the terms "open loop" and "closed loop": they use the term "open loop" to refer to discrete control systems, and the term "closed loop" to refer to continuous control systems; thus, because their system provides continuous control, they deem it a "closed loop" system. However, according to conventional practice (and for purposes of this disclosure), their system is actually an open-loop system, because the sensed variable (i.e. the exterior daylight level) is not affected by the setting of the blind.

In a closed-loop system, the sensed variable is directly affected by the shading setting, and the system adjusts the shading to reduce the difference between the measured and desired values of the sensed variable. For example, a closed-loop daylight control system might sense the daylight level inside the window—and then adjust the shading to maintain that level at some desired value.

One of the earliest such closed-loop systems is the automated window screen disclosed in U.S. Pat. No. 3,294,152 to Kuijvenhoven (1966). Kuijvenhoven shows a roller-type window shade, driven by a reversible electric motor, actuated in response to the light level measured by an inward-facing photoconductive cell mounted within a room. The shade is raised or lowered to maintain an approximately constant, user-specified level of daylight, as sensed by the photoconductive cell.

An advantage of sensor-based continuous-control systems is that they do not require "teaching" of predetermined shading settings (other than to define the bounds of the allowable shading range). Instead, these systems are equipped with input means to enable the user to specify a "set point" that defines the condition to be maintained (e.g. a desired level of daylight, analogous to the temperature set-point in a thermostat). The system—not the user—then determines the required shading setting to maintain the desired condition.

FIG. 4: Inconvenience Associated with Sensor-Based Continuous Control System

FIG. 4 shows a plot of estimated inconvenience versus time for a sensor-based continuous-control automated shading system. This system requires no programming, so that it does not incur significant short-term inconvenience.

However, users typically do not want a particular shading-determined condition—e.g., a desired level of daylight—to be maintained indefinitely. Rather, users typically prefer different shading-determined conditions at different times. For example, a user might desire a constant level of daylight during work hours, but prefer full shading (for privacy) at nighttime. Pure continuous control systems, as described above, cannot anticipate such changing preferences. Thus, sensor-based continuous-control systems do not substantially reduce the long-term inconvenience associated with deliberate shading adjustments.

Clock-Based Systems

A clock-based system adjusts the shading to predetermined settings at predetermined times (and, optionally, on predetermined days). Each such shading "event" must be taught to the system before use. This typically entails entering the time and shading setting for each desired shading event, via a keypad, in a process similar to that used in programming alarm clocks or early Video-Cassette Recorders (VCR's).

Examples of such systems include the automated shading systems manufactured by Somfy Systems of Cranbury, N.J., that include that the optional Chronis RTS Timer.

FIG. 5: Inconvenience Associated with Clock-Based System

FIG. 5 shows a plot of estimated inconvenience versus time for a clock-based automated shading system.

Such systems are most effective in buildings in which the occupants adhere to a rigid schedule, such as schools. FIG. 5 assumes such a building.

However, even in such buildings, clock-based systems suffer from the disadvantage that they cannot automatically adapt to changing conditions, such as changes in the weather or in the occupants' activities. Thus, while such systems can provide a noticeable reduction in long-term inconvenience associated with deliberate shading adjustments, they cannot substantially eliminate it. And such systems are even less effective in buildings in which the occupants do not always adhere to a rigid schedule, such as homes.

Further, clock-based systems can provide the level of effectiveness depicted in FIG. 5 only if the user programs a relatively large number of scheduled shading events; as shown in the figure, this results in substantial short-term inconvenience.

Summary of Prior-Art Limitations

As discussed above, prior-art automated shading systems suffer from one or both of two disadvantages:
 They are unable to substantially eliminate the long-term inconvenience of deliberate shading adjustments.
 They may require an inconvenient and intimidating programming or teaching process, thus causing substantial short-term inconvenience.

OBJECTS AND ADVANTAGES

It is therefore an object of my invention to provide an automated shading system which:
 Substantially eliminates the long-term inconvenience of deliberate shading adjustments, and
 Is easy to use (and, in particular, avoids the need for an inconvenient and intimidating "teaching" process), thereby minimizing short-term inconvenience.

Further objects and advantages will become apparent from a consideration of the drawings and accompanying description.

SUMMARY OF THE INVENTION

My invention consists of an innovative method of automated shading adjustment that can be implemented by conventional automated shading hardware, thus forming an innovative automated shading system.

The hardware consists of an electronically controlled shading device; sensing means for sensing at least two environmental characteristics; input means for registering deliberate shading commands from a user; and a control apparatus to register, store, and manipulate the outputs of the sensing means and input means, and to actuate the shading device, according to the innovative method of my invention.

A subsequent summary of my innovative method of shading adjustment makes reference to the following terms:
 Variable s represents a desired relative setting of the shading device. Variable s can range from 0% (minimum shading provided by the shading device, or fully open), to 100% (maximum shading provided by the shading device, or fully closed).
 Variable condition is a discrete (versus continuous) variable that characterizes the prevailing environment as a function of at least two environmental characteristics. Preferably, one of these characteristics is related to the exterior daylight level (e.g., as sensed by an outward-facing photocell), and another is related to the activities of the building occupants (e.g., the on/off state of the room lights, as sensed by an inward-facing artificial lighting sensor). Other environmental characteristics, such as the season (e.g. winter or summer), can also be arguments in the function that determines the value of condition. Because condition is a discrete variable, it has only a finite number of possible values.
 Variable state is a discrete variable that characterizes the history of the environmental condition as a function of the most recent N values of the condition. The parameter N can be thought of as the "depth" of the history of the environmental condition that is encoded by variable state. Because state is a discrete variable, it has only a finite number of possible values, ranging from 1 to J.
 Set {command(j): $1 \leq j \leq J$} is a set of automated shading command variables, containing one element command (j) for each of the J possible values of state, where j represents a value of state. Each command(j) defines the automatic shading adjustment, if any, to be performed when the value of state changes to j.
 Each command(j) can be of two types:
  An adjust_shading(s) command causes the shading device to be adjusted to relative setting s.
  A don't_adjust command causes no shading adjustment.
 With reference to the above terms, my innovative method of automated shading adjustment includes the following steps (performed in any order, unless otherwise stated):
  Optionally initializing at least one member of set {command(j):} to a don't_adjust command.
  Optionally initializing at least one member of set {command(j):} to an adjust_shading(s) command, where s represents a predetermined desired setting, typically 0% or 100%.
  Performing the following actions in response to each deliberate shading command registered on the input means:
   Adjusting the shading device to increase or decrease the shading according to the deliberate shading command, and subsequently
   Making command(j) an adjust_shading(s) command, where j represents the current value of state and s represents the new relative setting of the shading device.
  After any change in state, executing the corresponding command(j) where j represents the new value of state.

Thus, according to my method, there is no need for a deliberate teaching process: the user simply adjusts the shading, when desired, via deliberate shading commands. The system associates the value of relative shading setting s after each deliberate shading adjustment with the prevailing value of state. Subsequently, whenever the same value of state occurs, the system automatically adjusts the shading to the associated value of s.

As deliberate shading adjustments are made for different values of state, the system learns more and more about the user's shading preferences. Within a relatively short period of time (just a few days, in some applications), the system will have learned enough to automatically provide the desired shading under most conditions, thereby substantially reducing the need for further deliberate shading adjustments.

In fact, testing shows that my system is significantly more effective than the prior art in reducing both the short-term and long-term inconvenience associated with deliberate shading adjustments. At the same time, my system can be implemented using simple and inexpensive hardware.

As I teach in this disclosure, these advantages are due to innovation in the number and type of sensed environmental characteristics, as well as two key innovations that further distinguish my invention over the prior art:

Unlike prior-art sensor-based discrete control systems, my invention optionally exploits the history of recent changes in the environmental characteristics, rather than just the prevailing characteristics. This substantially improves the system's ability to anticipate users' shading preferences—and, thereby, substantially reduce the long-term inconvenience associated with deliberate shading adjustments—without significantly increasing the cost or complexity of the required hardware.

My innovative method of automated shading adjustment optionally includes the step of initializing at least one element of set {command(j):} to the don't_adjust command. As I teach herein, if every element of set {command(j):} is initialized to the don't_adjust command, then the short-term inconvenience is essentially the same as that of a mechanized (but non-automated system)—and therefore substantially less than that of prior-art automated systems. Further, as 1 also teach herein, if a judicious mix of don't_adjust and adjust_shading(s) commands are used to initialize set {command(j):}, then the short-term inconvenience can be reduced still further.

FORMAT CONVENTIONS

Figure 1:
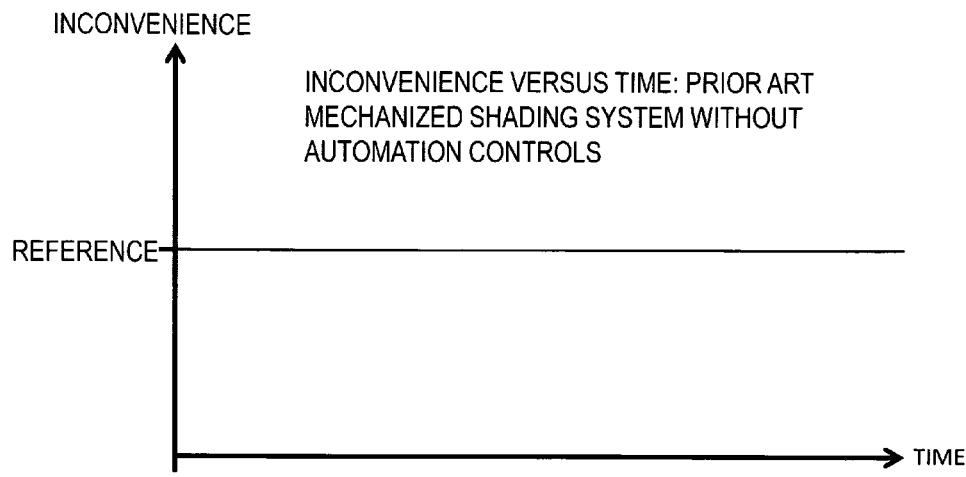
FIG. 1 is a plot of inconvenience versus time for a conventional mechanized shading device.
Figure 2:
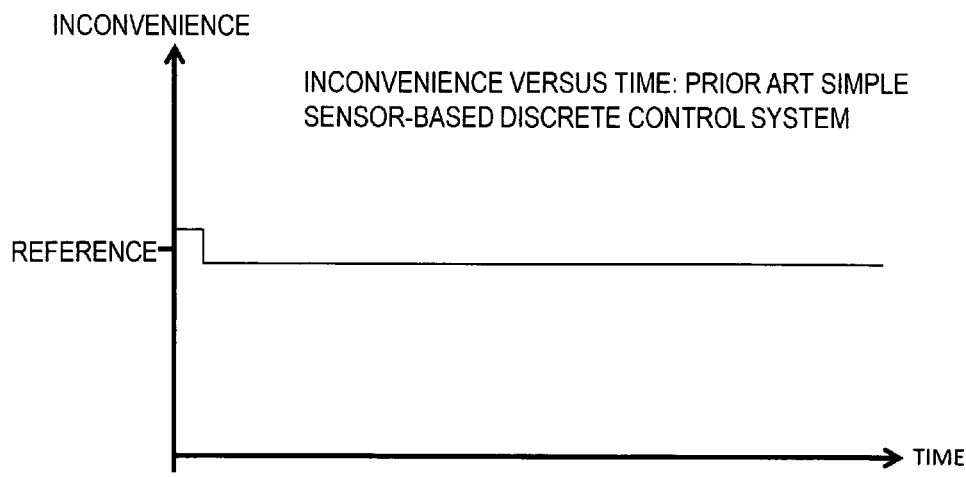
FIG. 2 is a plot of inconvenience versus time for a conventional automated shading device using simple sensor-based discrete control.
Figure 3:
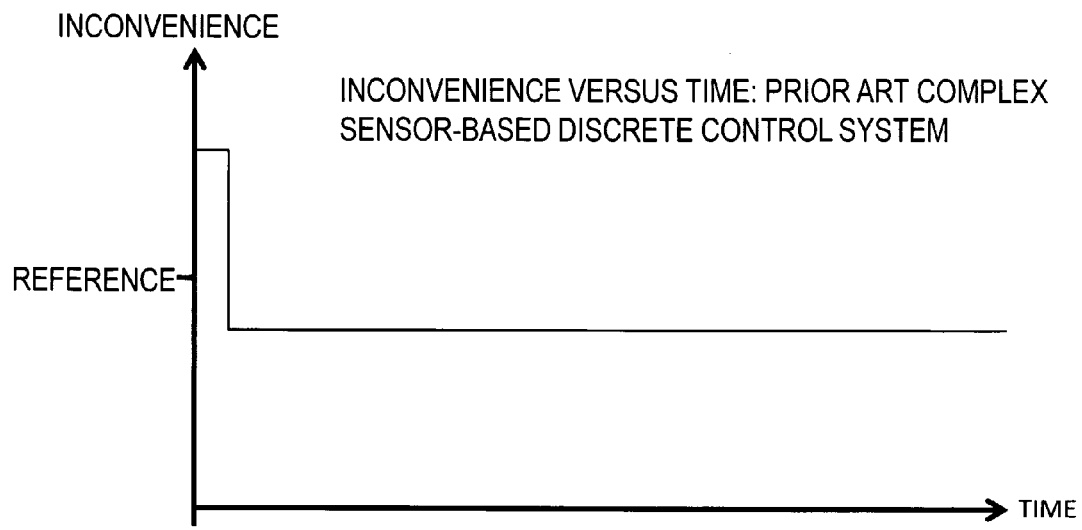
FIG. 3 is a plot of inconvenience versus time for a conventional automated shading device using complex sensor-based discrete control.

In this disclosure, I make reference to various variables, constants, and other special terms, as well as the reference numerals typically included in patent disclosures. The following formatting conventions are used in referencing these entities:

Reference numerals and corresponding descriptive phrases are indicated by bold typeface, e.g. "system 20".

Variables, constants, and other abstract entities are both italicized and bolded, e.g. "*variable name*".

Special terms and phrases are italicized, e.g. "*special term*".

All of these entities are listed for reference in the subsequent sections.

LIST OF REFERENCE NUMERALS

| | |
|---|---|
| 20 | Automated shading system |
| 21 | Electronically controlled shading device |
| 21A | Motorized window covering |
| 22 | Sensing means |
| 23 | User input interface |
| 24 | Control element |
| 24A | Microcontroller |
| 30-32 | Operating steps |
| 40 | Artificial light sensing means |
| 41 | External daylight sensing means |
| 42 | "Increase shading" signaling means |
| 43 | "Decrease shading" signaling means |
| 44 | "Set open/Lights On" signaling means |
| 45 | "Set closed/Lights Off" signaling means |
| 50 | Photodiode |
| 51 | Trans-impedance amplifier |
| 52 | High-pass filter |
| 53 | Detector |
| 54 | A/D converter |

-continued

| | |
|---|---|
| 55 | Photo-resistor |
| 56 | Capacitor |
| 57 | Resistor |
| 61 | Shade |
| 62 | Motor controller |
| 63 | Motor |
| 64 | Displacement sensor |
| 70 | Software initialization steps |
| 71-72 | Software steps |
| 80 | Software operating steps |

LIST OF CONSTANTS, VARIABLES, AND OTHER SPECIAL TERMS

For reference, the following list provides definitions of constants, variables, and other special terms and phrases referenced in this disclosure.

{command(j): $1 \leq j \leq J$} A set of J automated shading command variables, where J is the number of possible values of variable state. Thus, there is a one-to-one correspondence between the members of set {command(j): $1 \leq j \leq J$} and the members of the set of possible values of state.

For succinctness, set {command(j): $1 \leq j \leq J$} is also referred to herein in the abbreviated form {command(j):}.

adjust_shading(s) A value that can be assigned to any automated shading command(j) that causes shading device 21 to be automatically adjusted to relative shading setting s whenever state changes to a value of j.

For example, the following assignment causes shading device 21 to be closed (i.e. to provide 100% relative shading) when state changes to a value of j:
command(j)=adjust_shading(100%)

Adjust_shading(s) commands, with predetermined values of s, are assigned to selected members of set {command(j):} during system initialization. Thereafter, if a deliberate shading adjustment is made in state j when command(j) is an adjust_shading(s) command, the value of s is automatically updated to reflect the new relative shading setting.

adjust_without_update(s) Equivalent to adjust_shading(s), except that the value of s is not updated after a deliberate shading adjustment in the corresponding environmental state. Used only in alternative embodiments of system 20 to ensure that the default value of the corresponding command(j) is preserved.

Affordability A term referring to the inexpensiveness of the hardware required to implement system 20 command(j) A variable, contained in set {command(j):}, that represents the automated shading command to be performed when variable state changes to a value of j (in other words, whenever there is a state transition to state j).

condition A discrete variable characterizing the environment as a function of two or more environmental characteristics, e.g. as sensed by sensing means 22. For example, condition may be a function of lights and daylight.

condition_prev A discrete variable equal to the previous value of variable condition.

d A variable, used as an argument in a daylighting(d) command, representing the desired level of daylight in the room in which system 20 is located. Used only in alternative embodiments of system 20, e.g. for daylighting applications.

daylight A discrete variable representing the brightness of the daylight incident on outward-facing surface of shading device 21. Typically quantized to either two values (representing nighttime and daytime) or three values (representing nighttime, daytime, and direct sun). In the preferred embodiment, daylight is quantized to three values:
daylight=0 represents nighttime
daylight=1 represents daytime without direct sun
daylight=2 represents direct sun daylight_prev A discrete variable equal to the previous value of variable daylight.

daylighting(d) A value that can be assigned to any automated shading command(j) that causes shading device 21 to be automatically adjusted to maintain a desired interior daylight level d while state is equal to a value of j. After each deliberate shading adjustment in state j, the value of d is updated to the new interior daylight value. Used only in alternative embodiments of system 20, e.g. for daylighting applications.

Deliberate shading A term referring to a command initiated by a user, by actuating user input command interface 23, to cause a deliberate adjustment of shading device 21.

don't_adjust A value that can be assigned to any command(j) that is analogous to a software No Operation (NOP) command. For example, the following assignment results in no automatic shading adjustment of shading device 21 when state changes to a value of j:
command(j)=don't_adjust In the preferred embodiment, don't_adjust commands are assigned to selected members of set {command(j):} during system initialization. Thereafter, if a deliberate shading adjustment is made in state j when command(j) is a don't_adjust command, that command(j) is automatically changed to an adjust_shading(s) command, where s reflects the new relative shading setting.

don't_adjust_or_update Equivalent to don't_adjust, except that don't_adjust_or_update is not automatically changed to an adjust_shading(s) command after a deliberate shading adjustment in the corresponding environmental state. Used only in alternative embodiments of system 20 to ensure that the default value of the corresponding command(j) is preserved.

Effectiveness A term referring to the degree to which system 20 reduces the inconvenience associated with deliberate shading adjustments.

Fully taught A term describing the condition under which enough deliberate shading adjustments have been made so that set {command(j):} substantially reflects the user's shading preferences.

I A constant equal to the number of possible values of discrete variable condition. Constant I is a function of the number of environmental characteristics upon which condition is based, as well as of the level of quantization used in sensing those characteristics.

Inconvenience A term referring to the cognitive, sensory, and physical efforts associated with use of an automated shading system, such as system 20. This includes the short-term inconvenience due to the efforts required to program or set-up the system for use, as well as the long-term inconvenience due to the efforts required to make any deliberate shading adjustments that are subsequently necessary.

Initialization A term describing the process of setting each member of set {command(j):} to a predetermined default command.

J A constant equal to the number of possible values of discrete variable state. Constant J is a function of the number of possible environmental conditions I and the value of historical depth parameter N.

j A variable representing a value of state.

lights A discrete variable representing the on/off state of artificial lighting proximate to system 20. Typically quantized to two values, representing on and off. In the preferred embodiment,
lights=0 represents lights off
lights=1 represents lights on lights_prev A discrete variable equal to the previous value of variable lights.

N A parameter defining the depth of history of variable condition that is encoded in variable state. For example, if N=1, then state=condition; if N=2, then state is a function of the two most recent values of condition; if N=3, then state is a function of the three most recent values of condition, etc.

Reference Level A term referring to the inconvenience associated with use of a conventional mechanized (but non-automated) shading system. Such systems eliminate the physical, but not cognitive or sensory, effort associated with shading adjustments. The reference level refers to this residual cognitive and sensory effort.

s A variable, used as an argument in an adjust_shading(s) command, representing a relative shading setting of shading device 21. Variable s ranges from 0% (the minimum shading that can be provided by the shading device) to 100% (the maximum shading that can be provided by the shading device).

However, in alternative embodiments of system 20, variable s may represent an absolute (rather than relative) shading setting.

setting A variable representing the current absolute shading setting of shading device 21. In the case of the preferred embodiment, variable setting tracks the displacement of motor 63, which actuates shade 61, via displacement signals generated by displacement sensor 64. Unlike variable s, which has a defined range of 0% to 100% in the preferred embodiment, the minimum and maximum values of setting will depend on factors such as the design of shade 61 and sensor 64, as well as the height of the host window for shade 61.

In alternative embodiments, variable setting could track the drive voltage of a Smart Window based on Suspended Particle Device technology, the net energy applied to a Smart Window based on ElectroChromic Technology, or any other variable representing the control signal applied to, or absolute setting of, an electronically controlled window covering.

state A discrete variable characterizing the environmental state as a function of the most recent N values of condition. Thus, state captures the history of condition, with the parameter N defining the depth of that history.

State transition A term referring to a change in the value of variable state.

state_prev A discrete variable equal to previous value of variable state.

Teaching interval A term referring to the interval between initialization of set {command(j):} and the time at which system 20 becomes fully taught.

Conventions Regarding Descriptions of Operating Steps

In this disclosure I make reference to operating steps executed by or upon specific hardware. As is known in the art, such operating steps can be performed manually or executed automatically (e.g. via instructions that are hard-wired or encoded in software or firmware), and are typically described through the use of flowcharts. However, the operating steps associated with my invention involve direct and indirect manipulation of numerous constants and variables, making the use of flowcharts unwieldy. Accordingly, I use informal pseudo-code to describe the innovative operating steps associated with my invention. My pseudo-code uses plain-language words whose meaning will be clear to practitioners in the art, and adheres to the following conventions:

Constants, variables, and other abstract entities are denoted in the pseudo-code in the same manner as in the other portions of this disclosure, i.e. they are both italicized and bolded (e.g. "variable name").

Each comment is bounded by a forward slash and apostrophe (/*) at its beginning, and an apostrophe and forward slash at its end (*/).

Text is printed in the Arial font (in contrast to the Times New-Roman font as used in the balance of the disclosure), and is set-off from the other text via indentation.

The following is an example of my pseudo-code:

/* This is a comment line */
/* Initialize each of J commands in set {command(j):} to default values */
For q=1 to J
   /* Base each default value on the value of q */
   If value of q corresponds to (lights=1) AND (daylight=0) Then
     /* Value of q represents lights on during nighttime, so set default to 100% shading */
     Command(q)=adjust_shading(100%)
   Else
     /* Set default command to "don't adjust shading" */
     command(q)=don't_adjust
Next q For succinctness and clarity, my pseudo-code does not describe lower-level operations that are well known in the art. For example, I omit descriptions of switch polling and debouncing operations, as these are well established and will be familiar to any practitioner in the art.

DETAILED DESCRIPTION OF THE INVENTION

Principle of Operation

Detailed descriptions of preferred and alternative embodiments of my invention are provided in subsequent sections of this disclosure. This section provides a general description of my invention to facilitate understanding of its principle of operation, and notes the key considerations for its effective implementation.

Figure 6:
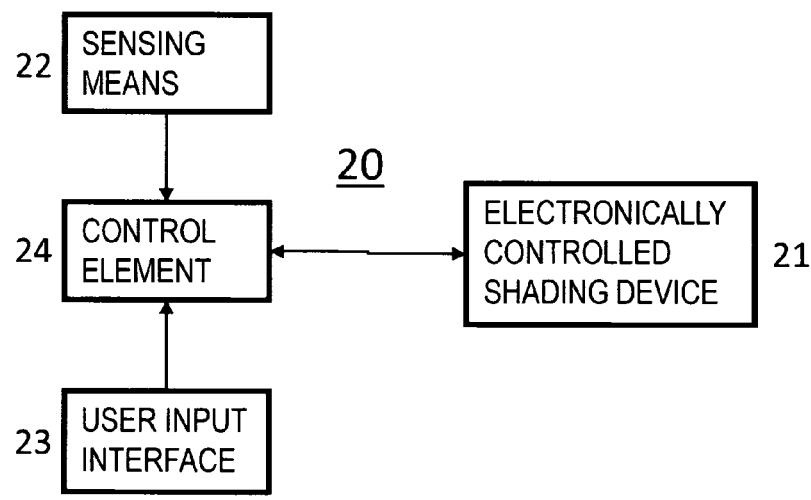
FIG. 6 is a functional block diagram of a general embodiment of an automated shading system according to my invention.

FIG. 6: Functional Block Diagram of System 20

FIG. 6 shows a functional hardware block diagram of a general embodiment of automated shading system 20 according to my invention. System 20 includes four functional elements: an electronically controlled shading device 21, sensing means 22, a user input interface 23, and a control element 24. Of course, practitioners in the art will recognize that a source of electrical power, such as a battery or AC-operated power supply, will also be present in embodiments of system 20; such a conventional power source is implied in FIG. 6, but omitted for the sake of clarity and simplicity.

Shading Device 21

Shading device 21 is any conventional device—such as a motorized window covering (e.g., a motorized horizontal blind or shade) or a "smart window"—capable of modulating the light passing through an aperture in response to an electronic signal.

Sensing Means 22

Sensing means 22 is a conventional device for characterizing the prevailing environment via discrete variable condition that is a function of at least two environmental characteristics that are directly or indirectly related to the need for window shading. Such characteristics could include, for example, the exterior daylight level, the artificial lighting level, room occupancy, the room temperature, the on/off state of various electronic equipment, and the prevailing season, among many others.

Accordingly, sensing means 22 could include sensors such as photocells, flicker detectors, thermistors, occupancy sensors, etc., along with appropriate means to derive discrete signals based on the outputs of those sensors. For example, it could include timing and control means to determine the length of the day, and hence the season, from the exterior daylight level. Further, sensing means 22 could also include an interface to the Internet to derive current weather information, from which a discrete visibility signal could be derived.

As I explain in a subsequent paragraph, the number and type of environmental characteristics sensed by sensing means 22 is an important consideration in achieving the most advantageous embodiment of my invention for a given application.

Because condition is a discrete variable, it can take on only a finite number of values I, where I is a function of the number of prevailing environmental characteristics and the quantization used in sensing those characteristics.

For example, sensing means 22 could comprise an outward-facing photocell and an inward-facing Passive InfraRed (PIR) occupancy sensor, along with associated comparator circuitry to generate a binary daytime/nighttime signal and a binary occupied/unoccupied signal. The value of condition could then be defined as the combination of these two binary signals, thus defining four possible values of condition, so that I=4.

As another example, sensor 22 could comprise a photocell, occupancy sensor, and temperature sensor, each driving an 8-bit A/D converter. In this case, because 8 bits define 256 possible values, I=256^3.

As I explain in a subsequent paragraph, the value of I is an important consideration in achieving the most advantageous embodiment of my invention for a given application.

User Input Interface 23

User input interface 23 is a conventional device capable of generating at least two signals in response to user inputs: a signal corresponding to an "increase shading" command and a signal corresponding to a "decrease shading" command. These commands are hereinafter referred to as deliberate shading commands. Input interface 23 may consist, for example, of a pair of momentary contact switches, or of an IR remote-control transmitter and receiver capable of transmitting and receiving, respectively at least two unique signals.

Control Element 24

Control element 24 is a conventional device for registering the sensor signals produced by sensing means 22 and the deliberate shading commands produced by user input interface 23, storing and recalling information, and actuating shading device 21 according to a predetermined method or algorithm. For example, control element 24 may be a conventional programmable microcontroller with internal or external memory.

Overall Configuration of System 20

Automated shading systems according to the functional configuration of system 20, as shown in FIG. 6, are well known in the art. For example, I show systems with such a functional configuration in my U.S. Pat. Nos. 5,598,000 (1997) and 5,760,558 (1998).

Figures 7, 8:
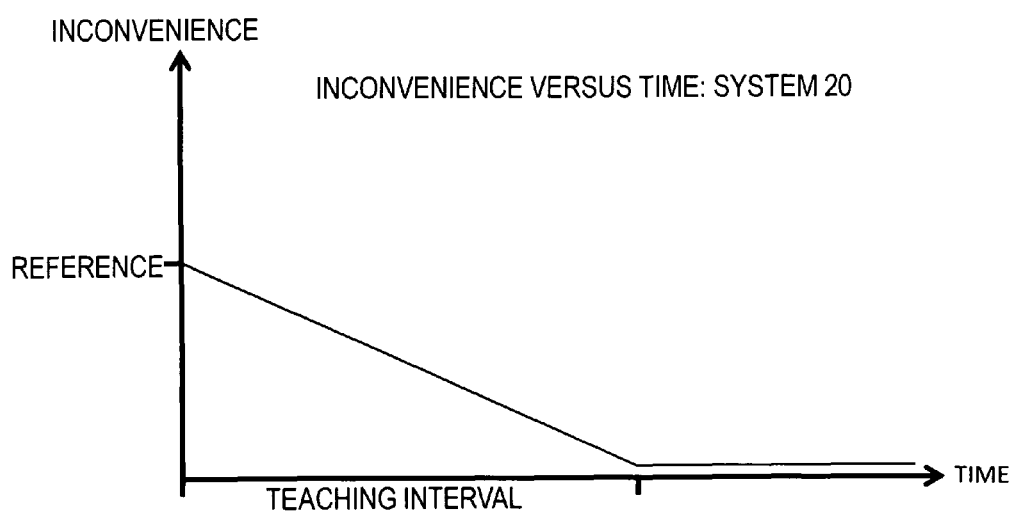
FIG. 7 is a high-level flowchart of the innovative operating steps of a general embodiment of an automated shading system according to my invention.
FIG. 8 is a plot of inconvenience versus time for a general embodiment of an automated shading system according to my invention.

FIG. 7: Method of Operation

According to my invention, system 20 previously shown in FIG. 6 performs an innovative method of automated shading adjustment. This method includes three major steps:

A step 30 to initialize a set $\{command(j): 1 \leq j \leq J\}$ of automated shading commands to default values.

A step 31 to detect and respond to changes in the value of environmental state variable state. Such changes are hereinafter referred to as state transitions.

A step 32 to detect and respond to deliberate shading commands registered on user input interface 23.

Step 30 is performed prior to usage of system 20, while steps 31 and 32 are performed upon each state transition and each deliberate shading command, respectively.

Step 30

Step 30 consists of the actions necessary to initialize the set of automated shading command variables $\{command(j):\}$ to default values.

There is a one-to-one correspondence between the members of set $\{command(j):\}$ and the set of possible environmental states, i.e., the set of possible values of state. Each member of set $\{command(j):\}$ is denoted as command(j), where j is the corresponding value of state, and where the value of command(j) defines the automated shading command to be executed upon a state transition in which the value of state changes to j. Because there are J possible values of state, the number of automated shading command variables in set $\{command(j):\}$ is also equal to J, ranging from command(1) to command(J).

Thus, step 30 involves initializing each command(j), where j ranges from 1 to J, to default values. Each command(j) can be initialized to one of two types of command:

An adjust_shading(s) command, which causes control element 24 to adjust shading device 21 to a relative shading setting of s. Thus, if command(j)=adjust_shading(s), then shading device 21 is adjusted to setting s whenever state changes to a value of j.

A don't_adjust command, which is analogous to a "no operation" command in computer science. Thus, if command(j)=don't_adjust, then no adjustment of shading device 21 is performed when state changes to a value of j.

The preferred procedure to determine the default value of each command(j) is discussed subsequently.

Step 31

Step 31 consists of the actions necessary to detect and respond to a state transition, i.e., a change in the value of state. The conventional steps required to detect such a change are not discussed herein, because such steps are well known in the art. For example, detection of such a change could be performed by periodically polling the output of sensing means 22, and evaluating the values of condition and state as a function of that output. Alternatively, a means of generating a "change" signal could be incorporated within sensing means 22 to trigger an interrupt in the operation of control element 24, which would then, in turn, evaluate the values of condition and state.

Step 31 further includes actions required execute automated shading command command(j) when a transition to state j is detected. For example, if command(j)=adjust_shading(s), then step 31 includes the actions required to adjust shading device 21 to setting of s when state changes to j. If, however, command(j)=don't_adjust, then no shading adjustment is performed in step 31.

Step 32

Step 32 consists of the actions necessary to respond to deliberate shading commands registered on user input interface 23 (previously shown in FIG. 6). The conventional steps required to detect such commands are not discussed herein, because such steps are well known in the art. For example, detection of such a command could be performed by periodically polling the output of interface 23, or by incorporating a means of generating a "change" signal within interface 23 to trigger an interrupt in the operation of control element 24.

Step 32 consists of the following actions:
- Adjusting the setting of shading device 21 (shown in FIG. 6) according to the deliberate shading command, and subsequently
- Changing the value of command(j), which may be either a don't_adjust or an adjust_shading(s) command, to an adjust_shading(s) command in which s represents the new relative setting of shading device 21.

Summary of Method of Operation

Thus, my innovative method of automated shading adjustment involves initializing each member of set {command(j): $1 \leq j \leq J$} to default values, so that each command(j) is either a don't_adjust or an adjust_shading(s) command. Thereafter,
- Whenever there is a state transition, the shading is adjusted according to command(j), where j is the new value of state.
- Whenever a deliberate shading command is registered, the shading is adjusted accordingly, after which the corresponding automated shading command is updated so that command(j)=adjust_shading(s), where j is the current value of state and s is the new relative shading setting.

Each deliberate shading adjustment can be viewed as a "lesson" which "teaches" system 20 the user's preferred shading setting in the current state. Eventually, after a sufficient number of deliberate shading adjustments, set {command(j):} will consist substantially of adjust_shading(s) commands that reflect the user's preferred shading settings, and the need for further deliberate shading adjustments will be greatly reduced (and even virtually eliminated, depending on the implementation of system 20). When this occurs, system 20 is considered to be fully taught, and the interval between initialization and the time at which system 20 is fully taught is referred to as the teaching interval.

FIG. 8: Inconvenience Versus Time of System 20

FIG. 8 shows a plot of inconvenience versus time for system 20, analogous to the plots of prior-art systems shown in FIGS. 1 through 5. This shape of this plot differs significantly from those of FIGS. 1 through 5, due to four salient differences in the operation of system 20 relative to the prior art:
- System 20 requires no dedicated programming or teaching phase. Instead, it is ready to operate immediately after initialization.
- The inconvenience of system 20 is never greater than the reference level (which corresponds to the inconvenience associated with a mechanized, but non-automated, shading device).
- System 20 effectively "learns" the users' shading preferences via each deliberate shading adjustment made during the teaching interval. As a result, the required frequency of deliberate shading adjustments, and hence the inconvenience, decrease steadily during the teaching interval.
- After the teaching interval, system 20 reduces the frequency of required deliberate shading adjustments to near zero. Thus, system 20 virtually eliminates the long-term inconvenience associated with deliberate shading adjustments.

User Reaction to Duration of Teaching Interval

In comparing FIG. 8 to FIGS. 2, 3, and 5, it is evident that the teaching interval associated with system 20 is longer than the programming interval associated with conventional automated shading devices. The teaching interval can last for several days or even weeks, while the programming interval associated with conventional automated shading devices is usually measured in minutes (although the programming step must typically be repeated many times over the lifetime of such systems).

However, my research shows that, while users generally prefer a short teaching interval, they are also willing to accept a long teaching interval—up to several weeks or longer—provided that two criteria are met:
- The inconvenience at the beginning of the teaching interval must be no greater than the reference level.
- There must be a perceptible decrease in the level of inconvenience throughout the teaching interval.

Both criteria can be met by implementing system 20 according to the considerations discussed below.

Key Implementation Considerations

With reference to the general hardware configuration and method of operation described above, I now discuss key considerations in the implementation of my invention. In the following discussion, I make reference to two system attributes:
- Affordability refers to the inexpensiveness of the hardware required to implement system 20.
- Effectiveness refers to the degree to which system 20 reduces the inconvenience associated with deliberate shading adjustments.

These attributes are largely determined by four system design parameters:
- The number and type of environmental characteristics that define variable condition.
- The level of quantization of each sensed characteristic.
- The depth of history N.
- The procedure used to initialize set {command(j):} of automated shading commands to default values.

Number and Type of Environmental Characteristics Defining Condition

As previously noted, environmental state variable state is a function of the recent history of values of variable condition, which, in turn, is a function of prevailing environmental characteristics.

My testing shows that the number and type of these environmental characteristics are key determinants of the effectiveness of my invention in reducing the inconvenience associated with deliberate shading adjustments—as well as of the cost and complexity of the required hardware. In general, inconvenience decreases with the number of sensed characteristics, but so does affordability.

My testing has revealed the following general guidelines for choosing the type of environmental characteristics defining condition:
- The set of environmental characteristics should include a characteristic that is related to the external daylight level. This could be sensed, for example, by an outward-facing photocell mounted at the window.
- The set of environmental characteristics should include at least one characteristic that is directly or indirectly related to the activities of the building occupants. Such characteristics include, for example, room occupancy, the ambient temperature, the interior light level, the ambient sound-pressure level, and the states (e.g. on/off, brightness, volume, etc.) of various devices (e.g., lamps, televisions, computer monitors, etc.). The most preferable of these are the states of various devices, because such states appear to be more highly correlated with users' shading preferences than the other variables.
- Effectiveness can be further increased if additional environmental characteristics are sensed. However, to maximize effectiveness and affordability, the environmental characteristics defining condition should be causally uncorrelated. For example, if the set of characteristics includes the external daylight level and the on/off state of the artificial lighting system, then there is little benefit in also sensing the interior light level, because it is causally correlated to the other two characteristics. On the other hand, there would be significant benefit in also sensing the on/off state of a proximate television or the on/off state of a proximate computer monitor, because these characteristics can be expected to be causally uncorrelated to the exterior daylight level and (to a lesser extent) the on/off state of the lighting system.

My testing to date suggests that, if these criteria are met, substantial effectiveness can be obtained in many applications when just two characteristics are sensed, and in virtually all applications when three or four characteristics are sensed. Further, as will be evident in the subsequent description of preferred embodiments, this can be done using simple, inexpensive hardware.

Level of Quantization of Sensed Analog Characteristics

As previously noted, variable condition is a discrete variable that is a function of the sensed environmental characteristics. Each sensed characteristic may be inherently discrete (e.g., the on/off status of a television), or analog (e.g., the exterior daylight level). Since condition is a discrete variable, each sensed analog characteristic must be quantized before the value of condition can be evaluated.

As is known in the art, the coarsest quantization is single-bit quantization in which an analog signal is quantized to only two possible values. At the other extreme, analog signals may be quantized to an arbitrarily large number of values, e.g. 65,636 values via use of a 16-bit A/D converter. My invention is best implemented using relatively coarse quantization of each sensed analog characteristic, with the optimum quantization representing a balance between two conflicting criteria:

The minimum number of quanta should generally reflect the number of natural language descriptions used to span the expected analog range of the characteristic. This is based on the idea that language has evolved to reflect both the ability and the need for humans to resolve gradations in environmental characteristics (a similar criterion is used by some practitioners of fuzzy logic to define the number of "hedges" used in the "fuzzification" of crisp input values).

Consider, for example, the external daylight level, which has an expected minimum value corresponding to nighttime on a moonless night, and an expected maximum value corresponding to direct sun on a cloudless summer day. At the very minimum, this range could be spanned with just two natural language descriptions: "dark" and "bright". However, it is reasonable to hypothesize that most people would use a greater number of descriptions to span this range. To test this hypothesis, I conducted a simple experiment, with the following results:

Only a small percentage of people in my experiment used just two descriptions to span the range in expected daylight levels.

A greater percentage of people (though still a minority) used three descriptions to span the expected range: "dark", "bright", and "very bright".

Most people in my experiment used four descriptions to span the expected range: "dark", "barely dark/barely bright", "bright", and "very bright".

A few people used five descriptions to span the expected range: "very dark", "dark", "barely dark/barely bright", "bright", and "very bright".

Nobody used more than five descriptions to span the expected range.

Thus, according to my experiment, five-level quantization best reflects the typical person's ability and need to resolve the external daylight level, implying that the external daylight level should be quantized to at least five levels.

If this criterion is not met, system 20 will not be able to recognize as many discrete quanta as a typical user, and thus may not be able to substantially eliminate the need for deliberate shading adjustments due to changes in the quantized environmental characteristic.

On the other hand, the quantization must be coarse enough to substantially eliminate subjective ambiguity between the average values (mid-points) of adjacent quanta. For example, if the external daylight level is quantized to just two values—"dark" and "bright"—then there would be little subjective ambiguity between the average values of the quanta. As a result, there would be little risk that anyone would consider the midpoint of the "dark" quantum to be "bright"; conversely, there would be little risk that anyone would consider the midpoint of the "bright" quantum to be "dark".

However, if the external daylight level is quantized to five values—for example, "very dark", "dark", "barely dark/barely bright", "bright", and "very bright"—then there may be significant subjective ambiguity between adjacent quanta. For example, the midpoint of the "very dark" quantum may be considered "very dark" by most people, but only "dark" by others. Similarly, a particular individual may consider the midpoint of the same quantum to be "very dark" on one occasion, but only "dark" upon another occasion.

If the quantization is not sufficiently coarse to substantially eliminate this risk of subjective ambiguity, then system 20 may not be capable of substantially eliminating the need for deliberate shading adjustments—particularly when there are multiple users.

While these two criteria impose conflicting requirements on the quantization level, both can generally be met to a degree sufficient to ensure substantial effectiveness of system 20. For example, in the case of the external daylight level, high effectiveness results when two, three, or four-level quantization is used.

It should be noted that the quantization discussed above refers to the final quantization of analog characteristics to establish the value of condition. Of course, each characteristic could initially be quantized with much higher resolution. For example, the external daylight level could first be quantized to 256 values via an 8-bit A/D converter, and then re-quantized in software to a desired coarser quantization (e.g. three values) prior to evaluation of condition.

Potential Use of Clock/Calendar Data to Define Condition

While condition should be a function of sensed environmental characteristics, it could depend also on discrete variables derived from clock/calendar data. For example, in addition to the environmental characteristics discussed heretofore, condition could also be a function of the value of a weekday/weekend binary variable (which would indicate whether or not the current day is a weekday), or of the value of a summer/winter binary variable (which would indicate whether or not the prevailing season is summer).

However, my research to date suggests that, except in certain specialized applications, there is little benefit to including clock/calendar-based data in the definition of condition, and doing so could actually reduce the effectiveness of system 20. This is because users rarely prefer shading to be adjusted according to a rigid clock schedule. One potential exception is the case of a non-residential building in which automated shading is used to minimize summertime solar heating loads. In this case, it may be advantageous to add a discrete seasonal variable (such as a summer/winter binary variable) to the arguments of condition.

Further, use of clock/calendar-related data is potentially disadvantageous in that it would require a means of providing real-time clock/calendar information to system 20, and may also require an additional programming step to initialize the correct time of day and day of year. Of course, this disadvantage would not apply to embodiments of my invention that already include a real-time clock/calendar for other purposes.

Number of Possible Environmental Conditions

The number/of possible values of environmental condition variable condition is equal to the product of the numbers of possible quantized values of each sensed characteristic. For example, with two sensed characteristics and one-bit (i.e., two-value) quantization of each of those characteristics, I=4. As another example, with three sensed characteristics quantized to two values, three values, and four values, respectively, I=24.

In general, effectiveness appears to increase with increasing values of I, but increases more quickly with the number and type of sensed characteristics than with the level of quantization.

The required minimum value of/for effective operation of system 20 is defined indirectly by the aforementioned requirements on the number of sensed environmental characteristics and the required quantization levels. As previously noted, at least two characteristics should be sensed, and each should be quantized to at least two values; thus, $I \geq 4$ for effective operation. However, as previously noted, my testing to date suggests that there is little benefit in sensing more than four environmental characteristics and quantizing to more than four values. Thus, there is little benefit for I>256.

Depth of History N

Constant N defines the depth of history of the values of variable condition that are encoded in variable state. For example, if N=3, then state is a function of the three most recent values of condition.

Based on my testing to date, it appears that effectiveness increases with increasing N, up to at least N=3. In general, the value of N to obtain a given level of effectiveness will depend on the value of I, as well as on the number and type of sensed environmental characteristics that define variable condition.

Conversely, increasing the value of N can reduce the number of sensed environmental characteristics necessary to provide a desired level of effectiveness. This is significant because, unlike the number of sensed characteristics, N can be increased without a substantial increase in system cost or complexity. Specifically, increases in N require only a modest increase in the data storage requirements of control element 24. On the other hand, increases in the number of sensed characteristics can substantially increase the cost and complexity of sensing means 22, as well as increasing the data storage requirements of control element 24. For example, my research suggests that, when N=2, sensing of just three environmental characteristics can provide the same (or greater) effectiveness as a system in which N=1 and four characteristics are sensed.

My testing to date indicates that, depending on the system implementation, a high degree of effectiveness can be obtained for values of N ranging from 1 to 3.

Number of Possible Environmental States

The number J of possible environmental states is a function of the number/of possible values of variable condition and of the depth of history N. The specific function that determines J depends on the scope of possible state transitions.

If, for example, it is possible for every value of condition to transition directly to any other of the I values of condition, then J is equal to the number of permutations of N values of condition from the set of I possible values, so that:

$$J = (I!) \div (I-N)!$$

If, however, it is not possible for every value of condition to transition directly to any other value of condition, then J will be smaller than that given by the above equation.

For example, the scope of possible state transitions will be constrained when an environmental characteristic is quantized to more than two values. If, for example, the exterior daylight level is quantized to three values representing nighttime, daytime, and direct sun, then condition cannot transition directly from the "nighttime" value to the "direct sun" value; it must first pass through the "daytime" value.

Minimum Value of J

As discussed in the preceding paragraphs, there are certain minimum requirements on the number I of environmental conditions, and on the depth of history N, in order to ensure the desired effectiveness of system 20. These minimum requirements, in turn, indirectly impose a requirement on the minimum value of J.

Sufficient testing has not yet been done to establish firm requirements on the minimum value of J. However, testing to date suggests a minimum value of 4 to 8 in order to achieve acceptable effectiveness in most applications.

Maximum Value of J

As previously noted, effectiveness increases with increasing values of I and N; thus, effectiveness should also increase with increasing J. Preliminary testing has verified this; effectiveness does appear to increase with increasing J, up to at least J=24.

However, there are two factors that could establish an upper limit on the optimum value of J.

First, increasing the value of J increases the memory requirements associated with control element 24. This will generally not be a limiting factor, because memory is relatively inexpensive. However, it may be a consideration for highly constrained implementations of control element 24.

Second, increasing the value of J increases the teaching interval (this is especially true when the increase in J is due to an increase in the depth of history N). This is due to the fact that, in order for the system to be fully taught, enough time must elapse so that the user has the opportunity to make a deliberate shading adjustment in substantially every state, if so desired. As previously noted, a longer teaching interval is disadvantageous only if (1) the inconvenience associated with system operation is initially greater than the reference level, or (2) the inconvenience does not decrease steadily and perceptibly over the teaching interval. Both of these criteria can be avoided via a judicious selection of default automated shading commands, as described subsequently.

Procedure for Initialization of Automated Shading Commands

As previously noted, my method of automated shading adjustment includes step 30 of initializing set {command(j): $1 \leq j \leq J$} of automated shading command variables to predetermined default values, so that each command(j) is set to either a don't_adjust or an adjust_shading(s) command.

Use of "Don't Adjust Shading" Defaults

If every member of set {command(j):} is initialized to a don't_adjust command, then system 20 initially behaves as an ordinary mechanized (non-automated) shading system, so that all shading adjustments must be made deliberately by a user. Each deliberate adjustment causes the value of command(j), where j is the current value of state, to be changed from a don't_adjust command to an adjust_shading(s) command, where s is the new relative shading setting. In this way, system 20 gradually makes the transition to fully automated operation as the teaching interval progresses.

Thus, if every member of set {command(j):} is initialized to a don't_adjust command, then the level of inconvenience immediately after initialization is no greater than the reference level—i.e., the level associated with a mechanized (but non-automated) shading device (as previously shown in FIG. 1).

Use of "Adjust Shading" Defaults

In the event that the user's preferred shading setting for a particular value of state is known at the time of initialization of set {command(j):}, then the corresponding value of command(j) can be initialized to the appropriate adjust_shading(s) command. The system would then automatically provide the correct shading in that state, with no need for deliberate action by the user. Each such adjust_shading(s) command would shorten the teaching interval, so that if every value of command(j) were initialized to an appropriate adjust_shading(s) command, the teaching interval would be eliminated, and the system would be fully taught immediately after initialization.

If, however, an adjust_shading(s) command does not correctly reflect a user's shading preferences, the user would be forced to make a deliberate shading adjustment to correct the shading setting. Each such incorrect adjust_shading(s) command would increase the level of inconvenience during the teaching interval.

Figure 9:
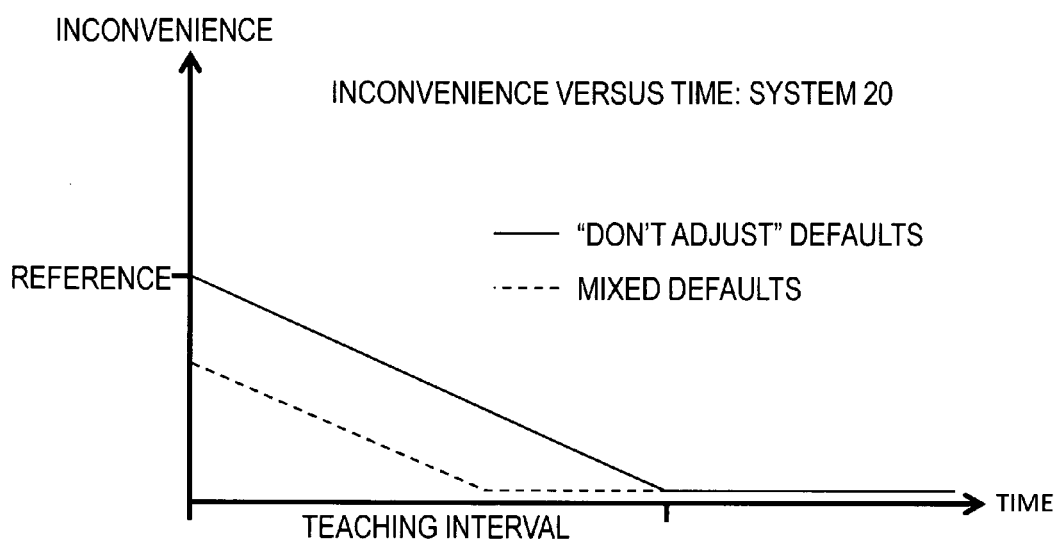
FIG. 9 is a plot of is a plot of inconvenience versus time for a general embodiment of an automated shading system according to my invention, showing the difference between use of don't_adjust default automated shading commands and use of a mixed set of default commands.

FIG. 9: Use of Mixed Defaults

For the reasons described above, it will generally be advantageous to use a mix of adjust_shading(s) and don't_adjust command defaults. Mixed defaults (i.e., a mix of adjust_shading(s) and don't_adjust command defaults) can provide two benefits:

To the extent that the defaults include adjust_shading(s) commands that correctly anticipate the user's preferences, a set of mixed defaults can significantly reduce the initial level of inconvenience, while also shortening the teaching interval.

Mixed defaults can ensure that other high-priority shading criteria are immediately met. For example, in a non-residential building, it may be desirable to fully shade the window of an unoccupied room during the daytime, in order to minimize the solar heating load on the building's climate-control system. Because the room is unoccupied, no user would be present to make a deliberate shading adjustment to teach the system the correct setting. This problem can be solved by use of the appropriate adjust_shading(s) command default, causing system 20 to automatically provide the correct shading without requiring any deliberate action or teaching by a user.

Procedure to Establish Defaults

The following is one advantageous procedure to establish default automated shading commands for the initialization process:

For states in which the preferred shading settings are known with a high degree of confidence, the corresponding automated shading command variables are initialized to the appropriate adjust_shading(s) commands. These preferred shading settings could be based on known user preferences, or on other criteria (such as the desire to minimize solar heating, as previously mentioned).

Known user preferences could be determined from data collected in a test program, or from data collected in actual installations of other instances of system 20.

For states in which the preferred shading settings are unknown (or known with a low degree of confidence), the corresponding automated shading command variables are initialized to don't_adjust commands.

For states in which the preferred shading settings are known to only a medium degree of confidence, the corresponding automated shading command variables are initialized to either adjust_shading(s) or don't adjust commands, according to the following procedure:

As previously noted, variable condition is preferably a function of at least one environmental characteristic related to occupant activity. For states in which the most recent value of condition is associated with occupant activity, the corresponding automated shading command variables are initialized to don't_adjust commands.

Automated shading command variables for the remaining states are initialized to an appropriate adjust_shading(s) command.

Other procedures to establish defaults are discussed elsewhere herein, under "Alternative Embodiments"

Description of Preferred Embodiment

As this disclosure makes clear, my invention supports a wide range of advantageous embodiments. The preferred embodiment will depend on the specific requirements of the application at hand, and may be optimized for that application using the information provided herein. For illustrative purposes, the following paragraphs describe a preferred embodiment for one significant commercial application.

Target Application

An important commercial application for my invention is mass-market automated shading for residential buildings. My research shows that an automated shading product capable of penetrating the mass market must virtually eliminate the long-term inconvenience associated with deliberate shading adjustments, without incurring the short-term inconvenience of an intimidating programming process—while being significantly more affordable than conventional automated shading products. My invention makes this possible.

Design Parameters

In accordance with the guidelines discussed previously, the preferred embodiment of my invention has the following design parameters:

Variable condition is a function of two sensed environmental characteristics: the external daylight level and the on/off state of the room lights.

The external daylight level is quantized to three levels (representing nighttime, daytime, and direct sun), while the state of the room lights is quantized to two levels (representing on and off). The quantized external daylight level is represented by discrete variable daylight, which has three possible values, while the lighting state is represented by variable lights, which has two possible values. Thus, there are six possible values of condition, so that I=6.

The value of historical depth parameter N=2. Thus, variable state is a function of the two most recent values of condition. This results in 40 theoretically possible values of state, so J=40 (however, some of these values will never occur in practice, because variable daylight cannot transition directly from nighttime to direct sun without first passing through daytime).

These parameters provide a high degree of effectiveness in minimizing the need for deliberate shading adjustments—but nevertheless enable a highly affordable implementation.

Figure 10:
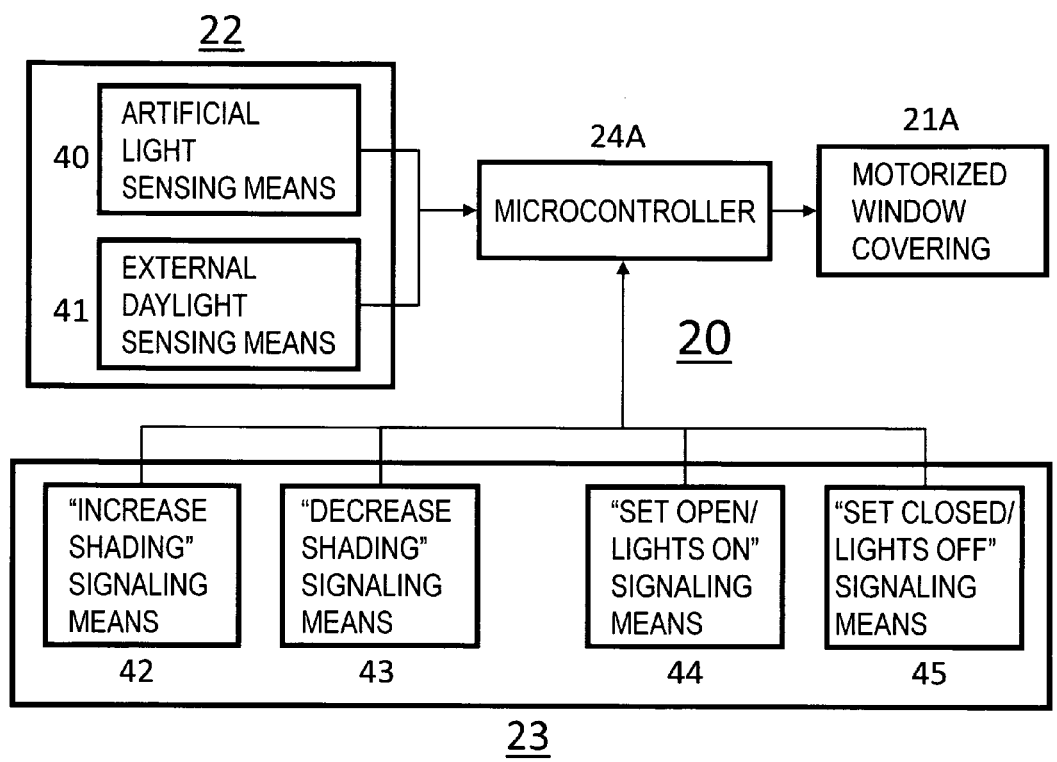
FIG. 10 is a block diagram of a preferred embodiment of an automated shading system according to my invention.

FIG. 10: Block Diagram of Preferred Embodiment of System 20

FIG. 10 shows a block diagram of a preferred embodiment of system 20. This diagram is consistent with the general diagram shown in FIG. 6, but highlights three specific features of the preferred embodiment:

In accordance with the design parameters described above, sensing means 22 consists of conventional artificial light sensing means 40 and conventional external daylight sensing means 41.

User input interface 23 consists of conventional "increase shading" signaling means 42, conventional "decrease shading" signaling means 43, conventional "set open/lights on" signaling means 44, and conventional "set closed/lights off" signaling means 45.

Control element 24 consists of conventional microcontroller 24A.

Electronically controlled shading device 21 is a conventional motorized window covering 21A.

Of course, practitioners in the art will recognize that a source of electrical power, such as a battery or AC-operated power supply, will also be present in embodiments of system 20; such a conventional power source is implied in FIG. 10, but omitted for the sake of clarity and simplicity.

Figure 4:
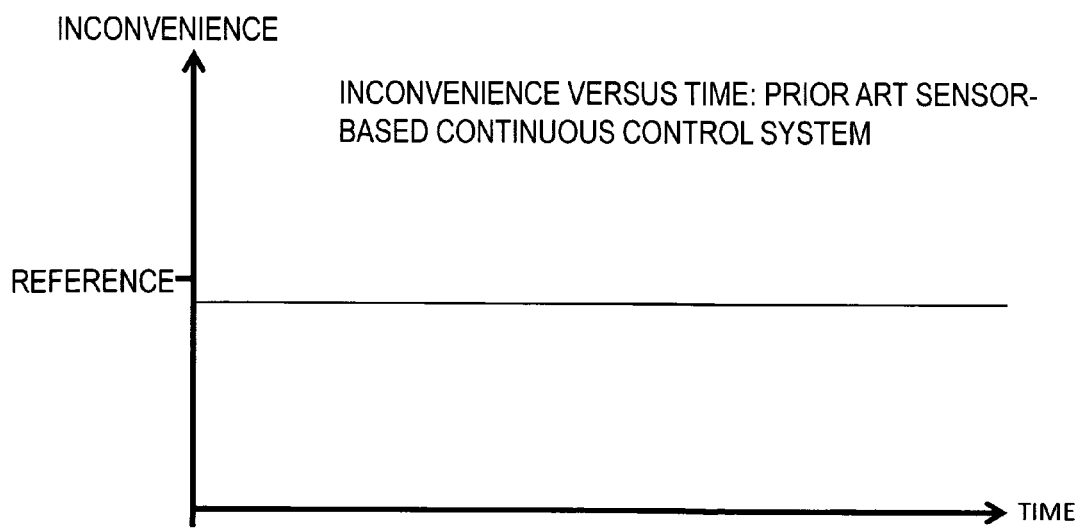
FIG. 4 is a plot of inconvenience versus time for a conventional automated shading device using sensor-based continuous control.
Figure 5:
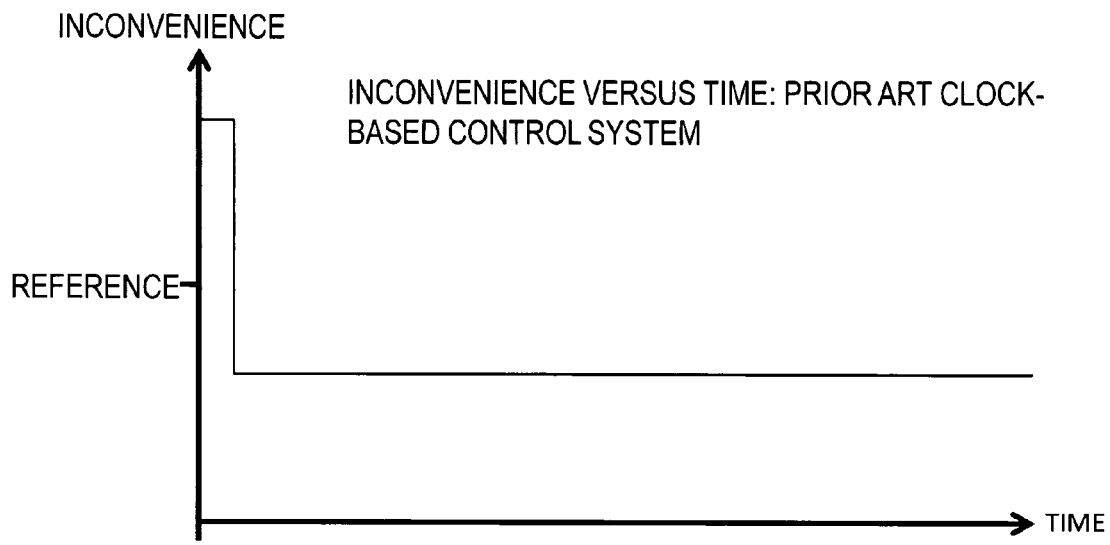
FIG. 5 is a plot of inconvenience versus time for a conventional automated shading device using clock-based control.

The configuration depicted in FIG. 10 is similar to that of the hardware configuration of the Dual-Mode Automatic Window Covering disclosed in my U.S. Pat. No. 5,598,000 (1997), particularly as shown in FIG. 4 of that disclosure.

Figure 11:
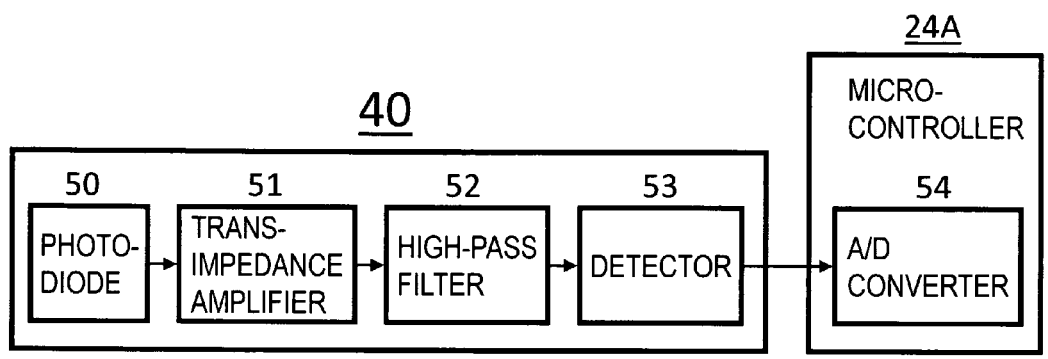
FIG. 11 is a block diagram of conventional artificial light sensing means per a preferred embodiment of an automated shading system according to my invention.

FIG. 11: Artificial Light Sensing Means 40

Artificial light sensing means 40 is a conventional apparatus that generates a signal representing the on/off state of artificial lighting in the area in which system 20 is located.

Several conventional approaches for sensing the on/off state of artificial lighting are described in the prior-art discussion of my aforementioned U.S. Pat. No. 5,598,000. One approach involves the use of a current sensor to sense the supply current driving the lamp; another involves the use of a light sensor that is shielded, located, and oriented to sense the light produced by the artificial lighting source while substantially ignoring light from other illumination sources.

In addition, in said patent I teach that such sensing can be advantageously accomplished with a simple, inexpensive apparatus that detects the flicker (i.e., the time-varying component) of the illumination produced by AC-powered lamps, and I disclose various embodiments of such an apparatus. Use of such a flicker detector eliminates the need for a physical connection between system 20 and the source of artificial illumination. Further, there are no special requirements with respect to shielding, location, and orientation of such a flicker detector.

For these reasons, the preferred embodiment of the instant invention implements artificial light sensing means 40 as a conventional flicker detector. As shown in FIG. 11, it consists of the following:

A photodiode 50 is a conventional silicon photodiode.

A trans-impedance amplifier 51 is a conventional amplifier that converts the photocurrent generated in photodiode 50 into a voltage.

A high-pass filter 52 is a conventional filter, either passive or active, that passes only signals with a frequency above a predetermined value.

A detector 53 is a conventional device, such as an active or passive rectifier, for producing a DC signal corresponding to the amplitude of, or power associated with, an AC waveform.

The output of artificial light sensing means 40, taken from detector 53, drives a conventional A/D converter 54 within microcontroller 24A. The output of A/D converter 54 represents the amplitude of the flickering portion of the illumination incident on photodiode 50; microcontroller 24A compares this amplitude to a single predetermined threshold to infer the on/off state of room lighting. In the preferred embodiment, the predetermined threshold is user-adjustable via a process to be described subsequently.

Design Considerations

There are three primary considerations that affect the design of artificial light sensing means 40:

The required sensitivity, which depends on the minimum illuminance of the artificial illumination to be detected. This, in turn, depends on the radiant power of the artificial light source, as well as on the orientation and location of photodiode 50 relative to the source.

The frequency of the flicker inherent in the artificial illumination to be detected. This depends on the type of light source, and typically ranges from twice the AC powerline frequency (for incandescent lighting and magnetically ballasted fluorescent lighting), to several tens of kilohertz or higher (for electronically ballasted fluorescent lighting and pulse-width modulated lighting using Light-Emitting Diode lamps).

The maximum illuminance of the non-flickering component of the net (artificial plus natural) ambient illumination. While some artificial light sources have a significant non-flickering component, the maximum non-flickering illuminance is typically determined by the amount of daylight reaching photodiode 50.

As will be appreciated by practitioners in the art, the design of artificial light sensing means 40 is facilitated when the required sensitivity, flicker frequency, and maximum non-flickering illuminance are all relatively low. Fortunately, this is the case for the preferred embodiment:

My research shows that effectiveness of system 20 is maximized when the output of artificial light sensing means 40 depends on the on/off state of the proximate area-lighting system, but is relatively insensitive to the on/off states of proximate task-lighting or accent-lighting systems. This criterion tends to reduce the required sensitivity of artificial light sensing means 40, because area-lighting systems produce substantially more radiant power than other sources of artificial illumination—and that power is distributed over a relatively wide angular range.

Conventional incandescent lighting still dominates residential lighting in the USA. Incandescent lighting produces flicker at twice the powerline frequency (120 Hertz in the USA)—a frequency that is far lower than the frequency of flicker produced by electronically ballasted fluorescent lighting or pulse-width controlled lighting using Light-Emitting Diode (LED) lamps. This means that sensing means 40 can be designed with an effective bandwidth as low as 120 Hertz, which facilitates its design and enables the use of very inexpensive components. If other types of lighting are expected, sensing means 40 could require a bandwidth as high as several hundred kiloHertz, but even this is achievable with relatively inexpensive components and straightforward conventional design techniques.

In the preferred embodiment of system 20, photodiode 50 is located in proximity to motorized window covering 21A—which, in turn, is located at a window—and faces inward, away from the window. As a result, photodiode 50 never receives direct solar illumination. This tends to minimize the maximum non-flickering illuminance, reducing the required dynamic range of sensing means 40 and further simplifying the design.

As a result, no special design techniques are required to implement sensing means 40 as depicted in FIG. 11; conventional design techniques may be used in accordance with the guidelines and considerations discussed above.

Figure 12:
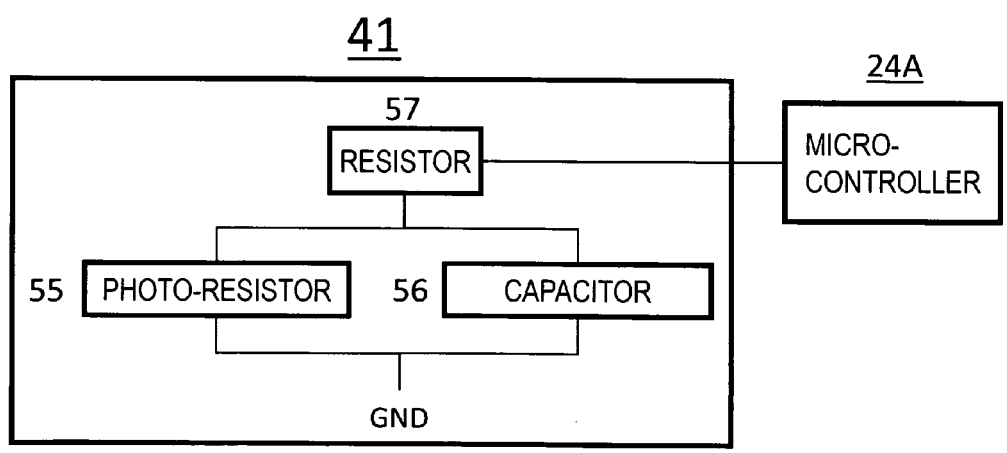
FIG. 12 is a block diagram of conventional external daylight sensing means per a preferred embodiment of an automated shading system according to my invention.

FIG. 12: External Daylight Sensing Means 41

As previously noted, external daylight sensing means 41 is a conventional device for sensing the level of daylight on the outward-facing side of motorized window covering 21A. Many such devices are known in the art; for example, my U.S. Pat. No. 5,760,558 (1998) discloses an automated shading system incorporating an outward-facing photo-resistor for this purpose, and many automated "dusk/dawn" lighting controls incorporating photo-resistors for this purpose are commercially available.

FIG. 12 shows a block diagram of a preferred embodiment of external daylight sensing means 41, which consists of a conventional Cadmium Sulfide (CdS) photo-resistor 55, conventional timing capacitor 56, and conventional current-limiting resistor 57 connected to a general-purpose I/O pin of microcontroller 24A. In this well-known configuration, microcontroller 24A measures the resistance of photo-resistor 55—and, hence, the brightness of the incident daylight—by measuring the RC time-constant of the series combination of capacitor 56 and photo-resistor 55. This is done via conventional software instructions executed by microcontroller 24A, by first configuring the I/O line as an output and bringing it high to fully charge timing capacitor 56 (with resistor 57 limiting the peak current). Then, the I/O line is re-configured as an input—allowing the capacitor 56 to discharge through photo-resistor 55—while measuring the time required for the voltage at the pin to reach the "low" logic threshold. This time is proportional to the resistance of photo-resistor 55, which in turn is proportional to the irradiance of the daylight incident on photo-resistor 55.

As previously indicated, the external daylight level is quantized to three values in the preferred embodiment of system 20, representing nighttime, daytime, and direct sun. This is done by comparing the measured resistance of photo-resistor 55 to two predetermined thresholds: a nighttime/daytime threshold, and a daytime/direct-sun threshold. In the preferred embodiment, these thresholds are predetermined at the factory, although they could be made user-adjustable in a conventional manner.

FIG. 10: Signaling Means 42 Through 45

In the preferred embodiment, user input interface 23 consists of signaling means 42 through 45. These are conventional momentary switches hardwired to microcontroller 24A (with conventional pull-up or pull-down resistors, if required), so that the latter registers actuation of signaling means 42, 43, 44, and 45 as "increase shading", "decrease shading", "set open/lights on setting", and "set closed/lights off setting" signals, respectively.

Figure 13:
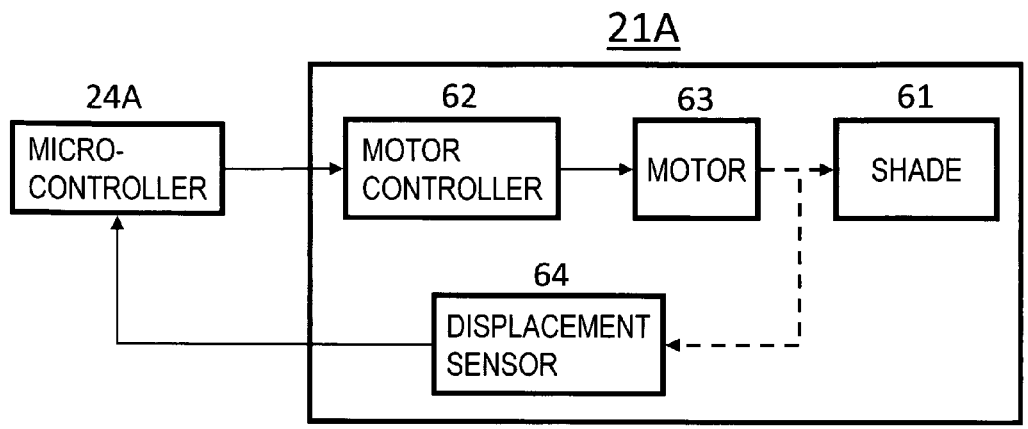
FIG. 13 is a block diagram of a conventional motorized window covering per a preferred embodiment of an automated shading system according to my invention.

FIG. 13: Motorized Window Covering 21a

In the preferred embodiment, motorized window covering 21A is a conventional motorized shade, consisting of the following elements:

A shade 61 is a conventional shade incorporating a control shaft, the rotation of which raises and lowers a shading device, thereby altering the degree of shading.

A motor controller 62 is a conventional device, such as an H-bridge, capable of providing bi-directional control of a DC motor in response to electronic control signals.

A motor 63 is a conventional DC gearmotor.

A displacement sensor 64 is a conventional device, such as an optical chopper, capable of registering the displacement of motor 63 and providing a corresponding displacement output signal.

The output shaft of motor 63 is physically coupled to the control shaft of shade 61 and sensor 64, so that displacement of motor 63 is registered by sensor 64 and causes adjustment of shade 61. Controller 62 is connected to motor 63 to control the operation of motor 63. Controller 62 and sensor 64 are connected to microcontroller 24A so that microcontroller 24A can issue control signals to controller 62 and register displacement signals produced by sensor 64.

Thus, motorized window covering 21A is a conventional servo-positioning system in which microcontroller 24A actuates motor 63, via controller 62, to substantially eliminate the difference between a desired setting of shade 61 and an actual setting, as registered by sensor 64. The actual setting of shade 61 is tracked via software variable setting. Unlike variable s, which has a range of 0% to 100%, the minimum and maximum values of setting will depend on the designs of shade 61 and displacement sensor 64, as well as the height of the host window.

Because the configuration depicted in FIG. 13 is very well known in the art (similar configurations are described, for example, in my U.S. Pat. Nos. 5,598,000 and 5,760,558), and because implementation details of window covering 21A are incidental to the innovations I disclose herein, I omit further discussion of such details for the sake of simplicity and clarity.

Operation of Preferred Embodiment

FIG. 10

General Hardware Operation

From a hardware standpoint, the operation of system 20 is similar to that of other automated shading systems known in the art, and operates in a conventional manner: microcontroller 24A monitors the outputs of sensing means 22 and user interface 23, and actuates motorized window covering 21A according to a predetermined program. In particular, microcontroller 24A adjusts window covering 21A in response to deliberate shading commands registered on interface 23 and in response to changes in the output of sensing means 22.

Figure 14:
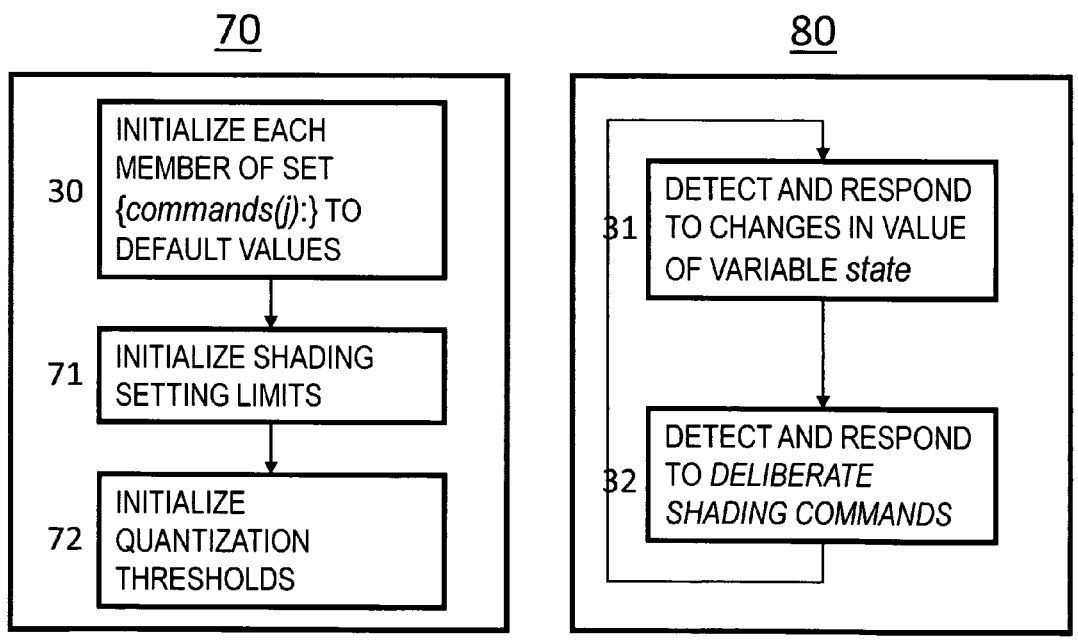
FIG. 14 is a high-level flowchart of the innovative operating steps of a preferred embodiment of an automated shading system according to my invention.

FIG. 14: Software Operating Steps

FIG. 14 lists the software operating steps associated with the preferred embodiment of system 20 according to my invention. The software operating steps are grouped into initialization steps 70 and operating steps 80. Steps 70 include previously referenced step 30, and steps 80 include previously referenced steps 31 and 32.

Initialization Steps 70

Initialization steps 70 are performed prior to usage of system 20 to prepare it for operation. They consist of aforementioned step 30, as well as conventional steps 71 and 72.

Step 30

As previously noted, Step 30 consists of operations to initialize the set of automated shading command variables {command(j):} to default values. Each of the J members command(j) of set {command(j):} is associated with a particular value j of state. Each command(j) is either an adjust_shading(s) or a don't_adjust command.

An advantageous procedure to establish default automated shading commands was discussed previously. The preferred embodiment uses a simplified version of that procedure: adjust_shading(s) default commands are used only for states in which the user's preferred shading setting is known (or can be predicted) with a high degree of confidence, and don't_adjust default commands are used for other states.

In the intended application for the preferred embodiment (automated shading in residential buildings), the only states in which users' preferred shading settings are predictable with a high degree of confidence are states in which the lights are "on" at nighttime. In such states, users generally prefer maximum, or fully closed, shading in order to maintain privacy. Accordingly, in the preferred embodiment, commands associated with such states are set to adjust_shading(100%), which cause microcontroller 24A to adjust motorized window covering 21A to provide maximum shading. For all other states, don't_adjust defaults are used. The following pseudo-code outlines the associated operations:

```
/* Step 30: Initialize each of J commands in set {command
   (j):} to default values */
For j=1 to J
   /* Base each default command on the value of j */
   If value of j corresponds to (lights=1) AND (daylight=0)
      Then
         /* Value of j represents lights on during nighttime, so
            set default command to maximize shading to main-
            tain privacy */
         command(j)=adjust_shading(100%)
      Else
         /* Set default command to "don't adjust shading" */
         command(j)=don't_adjust
      End If
Next j
Exit step 30
/* End of step 30 */
Step 71
```

Step 71 consists of a conventional sequence of operations to establish and store the values of variable setting corresponding to maximum and minimum shading settings of motorized window covering 21A. These values will be determined by the design of shade 61 and displacement sensor 64, as well as the height of the host window.

In essence, step 71 allows a user to deliberately adjust the setting of motorized window covering 21A, and then "tell" the system when the fully opened and fully closed limits have been reached. Such sequences of operation are well known in the art of motorized window coverings, and step 71 consists of such a conventional sequence:

```
/* Step 71: Initialize shading setting limits */
If signaling means 42 is actuated, then
   Actuate motor controller 62 to increase shading setting
      of shade 61
End If
If signaling means 43 is actuated, then
   Actuate motor controller 62 to decrease shading setting
      of shade 61
End If
If signaling means 44 is actuated, then
   Store current value of setting as minimum shading limit
      (0% relative shading)
End If
If signaling means 45 is actuated, then
   Store current value of setting as maximum shading limit
      (100% relative shading)
End If
If both signaling means 44 and 45 have been actuated since
      power-up, Then
   Exit step 71
End If
/* End of step 71 */
Step 72
```

Step 72 consists of a conventional sequence of operations to establish and store the values of thresholds associated with quantization of the discrete variables lights and daylight.

Thresholds for Variable Daylight

As previously stated, variable daylight is quantized to three values, representing nighttime, daytime, and direct sun. This requires two thresholds: a nighttime/daytime threshold, and a daytime/direct-sun threshold.

While it is possible to make these two thresholds user-adjustable, my tests have shown that fixed, factory-programmed daylight thresholds provide virtually the same system effectiveness. This is due to two factors:

The brightness of daylight varies over a wide range during transitions between nighttime and daytime, and between daytime and direct sun.

The rate of change of brightness over those transitions is relatively high.

As a result, significant changes in the value of the nighttime/daytime threshold have only a small effect on the clock time at which system 20 senses a nighttime/daytime transition. Similarly, significant changes in the value of the daytime/direct-sun threshold have only a small effect on the clock time at which system 20 senses a daytime/direct-sun transition.

Thus, these thresholds can be programmed at the factory, and will yield satisfactory operation in most cases. The thresholds can be determined according to conventional practice, based on characteristics (e.g. resistance versus irradiance) of photo-resistor 55.

Threshold for Variable Lights

As previously stated, variable lights is quantized to two values, representing on and off. Thus, only a single on/off threshold is required. Unlike the daylight thresholds, the optimum lights threshold will generally depend on specifics of the installation of system 20 (such as, for example, the type of area lighting system in use, as well as the relative location and orientation of photodiode 50). Thus, the lights threshold should be made user-adjustable in a conventional manner.

Sequences of operation to permit such a user-adjustable threshold are well known in the art, and step 72 includes such a conventional sequence for this purpose:

```
/* Set on/off threshold for variable lights */
If signaling means 44 is actuated, then
   Store reading of A/D converter 64 as "On" value
End If
If signaling means 45 is actuated, then
   Store reading of A/D converter 64 as "Off" value
End If
If both signaling means 44 and 45 have been actuated since
      power-up, Then
   Calculate threshold as average of "On" and "Off" values
   Exit procedure to set on/off threshold for variable lights
End If
/* End of step 72 */
```

Thus, to set the thresholds, the user simply turns the lights on and off, while actuating signaling means 44 when the lights are "on" and signaling means 45 when the lights are "off"; the threshold is then calculated as the average of the two values.

Operating Steps 80

Operating steps 80 consist of aforementioned steps 31 and 32. As shown in FIG. 14, these steps are executed in a loop, with step 31 executed before step 32. However, the ordering of steps 31 and 32 is arbitrary and incidental to the operation of system 20.

Operating Step 31

As previously stated, step 31 consists of the actions to detect and respond to a state transition, i.e. a change in the value of state. This includes evaluation of the environmental variables lights, daylight, and condition; evaluation of variable state as a function of the current and previous values of condition; and execution of the automated shading command command(j) associated with any new value j of state after a state transition. The following pseudo-code outlines the associated operations:

```
/* Step 31: respond to changes in state */
/* Save current values of state and condition */
    state_prev=state
    condition_prev=condition
/* Update values of environmental condition variables */
    /* Determine status of room lights */
        Read A/D converter 64
        Compare to lights on/off threshold
        Update value of lights accordingly
            /* Optionally apply hysteresis in conventional
              manner */
            lights=0 if below threshold
            lights=1 if above threshold
    /* Determine daylight status */
        Check external daylight level via sensing means 41
        Compare to daylight thresholds
        Update value of daylight accordingly
            /* Optionally apply hysteresis in conventional
              manner */
            daylight=0 if below night/day threshold
            daylight=1 if between night/day and day/direct-sun
              thresholds
            daylight=2 if above day/direct-sun threshold
    /* Determine the value of condition as a function of
      lights and daylight */
        /* This can be done using any mathematical function
          that produces a unique value of condition for each
          unique permutation of the values of the discrete
          arguments. Because lights has two possible values
          and daylight has three possible values, there are six
          possible values of condition. Thus, condition can
          be conveniently expressed as the sum of power-of-
          two-weighted values of lights and daylight */
        condition=1*lights+2*daylight
/* Determine value of state as a function of condition and
  condition_prev */
    /* This can be done using any mathematical function that
      produces a unique value of state for each unique per-
      mutation of the values of the arguments. Because
      condition and condition_prev each have six possible
      values, state can be conveniently expressed as the sum
      of one argument weighted by six and the other argu-
      ment weighted by one */
    state=1*condition+6*condition_prev
If state< >state_prev then
    Execute command(state)
        If command(state)=don't_adjust, then
            Do nothing
        End If
        If command(state)=adjust_shading(s) then
            /* Map desired relative shading setting (0% to
              100%) given by variable s to the corresponding
              value of variable setting. Do this by linear inter-
              polation across the range of variable setting
              established in step 71 */
            Map value of s to desired value of setting
            Adjust shade 61 to desired value of setting
        End If
End If
Exit Step 31
```

Note that, for succinctness and clarity, the pseudo-code above does not show the conventional lower-level operations required to determine the values of lights and daylight, or to actuate motorized window covering 21A to a desired value of setting. For example:

Determining the value of lights entails determining the output level of detector 53 using A/D converter 64 (see FIG. 11), and comparing said output level to a predetermined threshold, optionally using hysteresis. Similarly, determining the value of daylight entails charging capacitor 56, measuring the time required for it to discharge through photo-resistor 55 (see FIG. 12), and comparing that time to predetermined thresholds, optionally using hysteresis.

Actuating motorized window covering 21 to a desired value of setting entails actuating controller 62 to reduce the difference between the actual and desired values of setting to essentially zero.

Such operations are well known in the art and are incidental to the essence of my invention.

Operating Step 32

As previously noted, Step 32 consists of the actions necessary to respond to deliberate shading commands registered on user input interface 23. This includes actuation of motorized window covering 21A according to signals asserted by signaling means 42 or 43, as well as updating of the automated shading command within set {command(j):} that corresponds to the prevailing value of state. The following pseudo-code outlines the associated operations:

```
/* Step 32: respond to deliberate shading command */
/* Adjust shading if a deliberate shading command is
  asserted */
    If signaling means 42 is actuated, then
        Actuate motor controller 62 to increase shading set-
          ting of shade 61—but only if shading setting is less
          than maximum limit established in step 71
    End If
    If signaling means 43 is actuated, then
        Actuate motor controller 62 to decrease shading set-
          ting of shade 61—but only if shading setting is
          greater than minimum limit established in step 71
    End If
/* Update the automated shading command corresponding
  to the current value of state */
    /* Update command(j), where j is current value of state
      */
    /* Make new value of command(j) an adjust_shading(s)
      command that causes an automatic adjustment to the
      current value of setting upon each subsequent transi-
      tion to state j */
        /* Map value of setting into the corresponding value
          of s using linear interpolation, based on the range of
          variable setting (established in step 71) and the
          range of variable s (0% to 100%) */
        Map value of setting to a value of s
        /* Update command accordingly */
        command(j)=adjust_shading(s)
```

Exit step 32

Note that, for succinctness and clarity, the pseudo-code above does not show the conventional lower-level operations required to detect actuations of signaling means 42 and 43 or actuate motor controller 62, because such operations (e.g. polling or interrupt servicing, switch de-bouncing, motor control switching, etc.) are well known in the art.

Operation from User's Point of View

From the point of view of the user, system 20 is operated in exactly the same way as a conventional mechanized (but non-automated) shading device: the user simply adjusts the shading, when desired, via signaling means 42 and 43. The system "remembers" the shading setting after each such deliberate shading adjustment and associates it with the prevailing value of state. The system then automatically adjusts the shading to the same setting upon future transitions into that value of state.

As deliberate shading adjustments are made in different values of state, system 20 learns more and more about the user's shading preferences. Within a relatively short period of time (often just a few days), system 20 will have learned enough to automatically provide the desired shading under most conditions, thereby substantially reducing the need for further deliberate adjustments.

Advantages of Preferred Embodiment

FIG. 15

Inconvenience Versus Time for System 20 and Prior-Art

Figure 15:
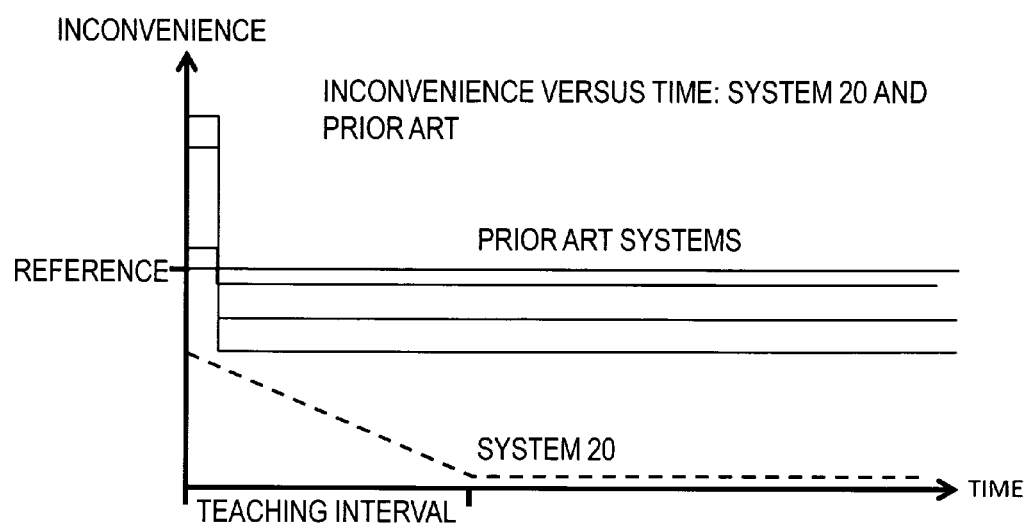
FIG. 15 is a is a plot of is a plot of inconvenience versus time for the preferred embodiment of an automated shading system according to my invention, as well as for prior-art automated shading systems.

FIG. 15 shows plots of inconvenience versus time for system 20, as well as for the various types of prior-art system described previously. Because system 20 requires no programming step prior to use, it avoids the short-term inconvenience caused by the prior-art automated systems. Further, because of its use of mixed defaults, it immediately reduces the inconvenience associated with deliberate shading adjustments to below the reference level—and continues to further reduce the inconvenience throughout the teaching interval.

Thus, system 20 avoids the trade-off between short-term and long-term inconvenience inherent in prior-art systems: its short-term and long-term effectiveness are both substantially greater than the prior art.

FIG. 10: Block Diagram of System 20

Further, despite the fact that system 20 is more effective than prior-art systems, FIG. 10 shows that it is no more complex than many prior-art automated shading systems, and can be implemented using inexpensive and readily available hardware.

Alternative Embodiments

My invention supports a wide range of useful alternative embodiments.

Alternative Design Parameters

As discussed previously, the affordability and effectiveness of embodiments of my invention are largely determined by four system design parameters:

The number and type of environmental characteristics that define variable condition. In the preferred embodiment, condition is a function of two sensed environmental characteristics: the external daylight level and the on/off state of the room lights.

The level of quantization of each sensed characteristic. In the preferred embodiment, the external daylight level is quantized to three levels, while the state of the room lights is quantized to two levels (representing on and off).

The depth of historical depth parameter N. In the preferred embodiment, N=2. Thus, variable state is a function of the two most recent values of condition.

The procedure used to initialize set {command(j):} of automated shading commands to default values. In the preferred embodiment, a simple procedure is used to initialize each command(j) to one of two default values: an adjust shading(100%) command (to fully maximize the shading) and a don't_adjust command, depending on the value of j.

The specific parameters selected for the preferred embodiment, as previously described, provide an excellent trade-off between affordability and effectiveness for mass-market residential applications. However, other combinations of parameters may be more appropriate for other applications. Elsewhere in this disclosure I discuss the appropriate ranges of each of these parameters, and the considerations involved in choosing them for a particular application.

For example, for a product targeted toward the premium or luxury segments of the residential market, it may be advantageous to trade some affordability for increased effectiveness. This could be done, for example, via the following:

Making variable condition a function of four (vice two) prevailing environmental characteristics: the external daylight level, the on/off state of the room lights, the on/off state of any proximate television, and the on/off state of any proximate computer monitor. One advantageous way to achieve this is to interface system 20 with a whole-house control system that controls lights, televisions, and computer monitors. Such a whole-house control system could "tell" system 20 the states of the various devices, functionally replacing (or greatly simplifying) sensing means 22.

Quantizing the external daylight to four (vice three) levels, representing nighttime, dusk/dawn, daytime, and direct sun; the state of the room lights to three (vice two) levels, representing off, dim, and bright; and the states of both the television and computer monitor to two levels, representing on and off.

Making the depth of history N equal to three (vice two).

Using a different procedure to establish the default values of each member of set {command(j):} of automated shading commands. The procedure used in the preferred embodiment assigns don't_adjust defaults to all states except those in which the lights are "on" at nighttime, in which case an adjust_shading(100%) default is assigned to provide maximum shading for the sake of privacy. However, it might be advantageous to also assign adjust_shading(100%) defaults for states in which direct sun is present. Alternative procedures for establishing default values of set {command(j):} are discussed more fully elsewhere herein, under "Alternative Methods of Operation"

Of course, such changes would require more memory within system 20 (to reflect the increased values of I and J), as well as appropriate modifications to the software of the preferred embodiment.

This combination of parameters will yield close to the maximum possible effectiveness, while still supporting an embodiment that is practical and affordable in the target market.

Alternative Hardware Configurations

As will be readily evident to practitioners in the art, my invention can be embodied with a wide variety of hardware configurations, consistent with the information disclosed herein.

Alternative Shading Devices

As previously noted, shading device 21 can be any electronically controlled shading device. Thus, motorized window covering 21A (which incorporates shade 61) of the preferred embodiment could be replaced with any other type of motorized window covering (such as those incorporating Venetian blinds or drapes), or with a Smart Window that has no moving parts. The choice of shading device, and the hardware considerations associated with its integration into system 20, are incidental to my invention and can be made according to conventional practice.

However, there are certain operational and software considerations in the use of my invention with alternative shading devices. These are discussed elsewhere herein, under "Alternative Methods of Operation".

Functionally Equivalent Hardware Alternatives

Of course, functionally equivalent hardware could be substituted for each of the hardware elements of the preferred embodiment. Examples of such substitutions include (but are not limited to) the following:

A conventional Infra-Red (IR) or Radio Frequency (RF) remote-control transmitter and receiver could be substituted for user input interface 23. Alternatively, signaling means 42 and 43 could be replaced by conventional voice-recognition means capable of recognizing spoken "brighten" and "darken" commands, and conveying the associated signals to microcontroller 24A. Alternatively, user input interface 23 could be replaced with a data interface to another control system (e.g. a home-automation system), enabling such a system to be used to issue commands to system 20.

Functionally equivalent sensing means could be substituted for the preferred embodiment of artificial light sensing means 40 (as depicted in FIG. 11). For example, the preferred embodiment of sensing means 40 could be replaced with one of the following:

A sensor that monitors the current or power consumed by a lighting system.

An interface to a lighting-control system to accept a signal indicating the status of the lighting system.

A conventional light sensor that is shielded, located, and oriented to sense the light produced by the artificial lighting system while substantially ignoring light from other illumination sources.

Functionally equivalent sensing means could be substituted for the preferred embodiment of external daylight sensing means 41 (depicted in FIG. 22). For example, the preferred embodiment of sensing means 41 could be replaced with one of the following:

A voltage divider formed by a fixed resistor and a photoresistor, with the output of the divider sampled by an A/D converter within microcontroller 24A.

A sensor to monitor the current supplied by a photovoltaic cell to a load, with the output of the sensor sampled by an A/D converter within microcontroller 24A.

Any other conventional light-sensing scheme, e.g. using photovoltaic cells, photodiodes, or phototransistors.

An interface to obtain local brightness information from another source, e.g. via the Internet.

Alternative Allocation of Functions to Hardware

Practitioners in the art will recognize that the allocation of functions to hardware elements depicted in FIGS. 6 and 20 represents only one of many possible allocations. For example, the functions allocated to microcontroller 24A in the preferred embodiment could, alternatively, be performed by a microprocessor or microcontroller contained within motorized window covering 21A, thereby eliminating the need for microcontroller 24A.

Similarly, the functions allocated to user input interface 23 could be performed by other input means contained within window covering 21A.

Subsumption within a Building Automation System

The hardware functions performed by system 20 could alternatively be performed by a conventional building-automation system. Such systems are capable of performing automated control of lighting, HVAC (heating, ventilation, and air-conditioning), entertainment, security, and window shading. For example, system 20 could be emulated by such a system in the following manner:

Such systems include at least one control element, e.g. a personal computer or an embedded control computer. Such a computer could functionally replace microcontroller 24A by performing the software operations described herein.

Such systems include at least one user input interface, e.g. keyboard, handheld remote control, touch-screen panel, etc. Such an interface could functionally replace user input interface 23.

Most such systems are capable of controlling lighting systems. As a result, such systems typically track the on/off status and brightness of lamps as software variables. In the context of my invention, such a software variable could functionally replace artificial light sensing means 40.

Most such systems are capable of being interfaced with an external daylight sensor, and many such systems already include such a sensor (or alternative means of obtaining brightness information, such as via local weather information obtained via the Internet). Such means could functionally replace external daylight sensing means 41.

Many such systems include electronically controlled shading systems. Such a motorized shading system could functionally replace motorized window covering 21A.

Thus, it will be evident to practitioners in the art that my invention can be readily embodied via software hosted on such a building automation system.

Alternative Methods of Operation

A variety of alternative methods of operation or software configurations can be used to implement my invention.

Alternative Functional Allocation Between Hardware and Software

As is known in the art, there are many possible ways to allocate a given function between software and hardware, and this is also the case with my invention.

For example, all of the software operations described herein, or a subset thereof, could be performed instead by firmware or hardware.

As another example, with reference to FIG. 11, trans-impedance amplifier 51 could be connected directly to A/D converter 64, with the high-pass and detection functions performed by digital signal-processing software within microcontroller 24A, eliminating the need for high-pass filter 52 and detector 53.

As another example, with reference to FIG. 10, the preferred embodiment uses four signaling means (signaling means 42 through 45) to enable the user to issue four unique signals to the system, which are then decoded by software into six unique commands (since each signal produced by means 44 and 45 can represent two possible commands). However, as is known in the art, additional software logic could be used to decode the required six commands from fewer signaling means (e.g. via detecting predetermined combinations or durations of signal actuations). Alternatively, additional signaling means could be provided (e.g. one signaling means for each of the six commands) to eliminate the need for software decoding.

Alternative Timing and Ordering of Steps 30, 71, and 72

As shown in FIG. 14, initialization steps 30, 71, and 72 are executed in a particular order. This order is based on, and may be altered according to, the following considerations:

- Step 30, in which members of set {command(j):} are initialized to a default values, can be executed at any time prior to usage of system 20 (i.e. at any time prior to execution of operating steps 80). Further, the operations associated with step 30 do not necessarily have to be performed by microcontroller 24A. For example, the operations could be performed by another computer (or even by a person), with the resulting default values of set {command(j):} then transferred into a memory device accessible by microcontroller 24A. This means that step 30 could be performed at the factory, even before system 20 is assembled.
- Step 71, in which the limits of variable setting are established, should be performed before usage of system 20, but after system 20 has been assembled and shade 61 has been installed on the host window. This is because the limits of setting will typically depend on the design of shade 61, as well as on the height of the host window. However, if another type of shading device is used, it may be feasible to perform step 71 prior to final installation of system 20. For example, if motorized window covering 21A is a motorized "tilt only" Venetian blind, then step 71 could be performed before final installation (but after system 20 is assembled), because the tilt limits of a Venetian blind depend only upon the design of the blind, and not on any characteristics of the host window.
- Step 72 consists of the sequence of operations to establish and store the values of thresholds associated with quantization of the discrete variables daylight and lights. These operations can be grouped into two categories: operations associated with establishing the daylight related thresholds, and operations associated with establishing the lights related threshold.
  - As previously stated, the daylight-related thresholds can be established at the factory, before final installation of system 20. Thus, while these operations are shown as being performed after steps 30 and 71, they could, in fact, be performed at any time after the characteristics of photo-resistor 55 are known, e.g. at the factory.
  - As previously stated, the lights-related thresholds will typically depend on the specifics of the installation of system 20 (such as the type and relative location of the proximate lighting system). Thus, these operations should typically be performed after installation of system 20.

Alternative Software Architectures and Algorithms

As is known in the art, a wide variety of software architectures and algorithms may be used to implement a given software functionality, and this is also the case with my invention.

Looping/Polling Versus Interrupts

For example, as shown in FIG. 14, operating steps 80 consist of steps 31 and 32 performed in a loop. However, as is known in the art, the same object could be achieved using an interrupt-oriented approach that causes steps 31 or 32 to be executed only when some predetermined condition occurs.

Similarly, when registering signals produced by sensing means 40 and 41 or signaling means 42 to 45, either a polled approach (in which each signal is periodically checked) or an interrupt-oriented approach (in which each sensing/signaling means generates an interrupt request when a predetermined condition occurs) could be used.

Determining Values of Environmental Conditions and States

As another example, the preferred embodiment of my invention uses a simple sum-of-weighted-values mathematical function to determine the value of condition as a function of lights and daylight. A similar sum-of-weighted-values approach is also used to determine the value of state as a function of condition and condition_prev. However, the specific function used to determine condition and state from its arguments is arbitrary and incidental to my invention, and other functions could be used. The only requirement is that the function should produce a unique output value for each unique permutation of the values of its arguments.

Elimination of Explicit References to Conditions and States

Discrete variable condition is a convenient way to represent one of a finite number of possible environmental conditions, while discrete variable state is a convenient way to represent a unique combination of the current and previous value(s) of condition. However, while the concept of discrete environmental conditions and states is key to my invention, it will be appreciated that condition and state do not necessarily have to appear as explicit variables in software used in embodiments of my invention.

In the preferred embodiment, condition is used as an argument for the function that determines state, and the value of state is used as an index to select an automated shading command from set {command(j):}. Also, in step 31, the value of state is tested to detect a change in environmental state.

However, changes in the environmental state could instead be detected by detecting changes in condition. And, since state is a function of condition and condition_prev, each automated shading command command(j), where j is a particular value of state, could instead be implemented as a two-dimensioned array variable, e.g. command(condition, condition_prev), thereby eliminating the need for variable state.

Further, since condition is a function of lights and daylight, changes in condition (and, therefore, state) could be detected by detecting changes in lights or daylight, and variable command(j) could be implemented as a four-dimensional array variable, e.g. command(lights, lights_prev, daylight, daylight_prev), where lights_prev and daylight_prev represent the previous values of lights and daylight, respectively. This would eliminate the need for variables condition and condition_prev.

Thus, while the concepts of condition and state are important, they do not necessarily have to appear as explicit variables. The choice between explicit and indirect reference to these variables can be made according to conventional software practice, given the characteristics of the software development environment and hardware used to implement system 20.

Alternative Procedures to Establish Default Automated Shading Commands

The process of initializing set {command(j):} of automated shading commands to default values is tantamount to predicting, where possible, the user's shading preferences in each environmental state. In the preferred embodiment, a simple rule is used in step 30 to establish the default values of each command(j). This rule, in essence, calls for an adjust_shading (100%) default value for all values of j for which lights=1 and daylight=0, and don't_adjust shading commands for all other values of j.

However, the specific procedure used to establish the defaults is incidental to my invention, and other advantageous procedures are possible.

Alternative Algorithms to Establish Defaults

As previously noted under "Alternative Design Parameters", other algorithms or rules to establish the default automated shading commands are possible. The following are examples of such rules:

"Provide maximum shading in the presence of direct sun". This rule would result in a default of adjust_shading (100%) for all values of j corresponding to daylight=2.

"Provide minimum shading during daytime, in the absence of direct sun, when the lights are 'on'". This rule would result in a default of adjust_shading(0%) for all values of j corresponding to lights=1 and daylight=1.

Many other such rules are possible. Such rules could be based on the preferences or opinions of the practitioner implementing system 20, on a survey of potential purchasers of system 20, or (most preferably) on objective information concerning actual user shading preferences in various environmental states. However, if sufficient objective information on user preferences is available, then it may be preferable to eschew algorithms or rules in favor of empirically derived defaults, as discussed below.

Empirically Derived Defaults

As an alternative to the use of algorithms or rules, the default commands could be established empirically. An advantageous way to obtain such empirically established defaults is from another, fully taught, instance of system 20, because set {command(j):} of a fully taught system will reflect actual user shading preferences for each value of j. As I discuss subsequently, system 20 could easily be modified to provide the capability to download such information to another device (such as a computer, another instance of system 20, or multiple instances of system 20, e.g. via an intranet or the Internet).

Indeed, near-optimal sets of default automated shading commands for various applications could be obtained by processing the values of set {command(j):}, downloaded from a large number of fully taught "source" instances of system 20, in various ways. Such processing could include, for example:

Binning the data according to the type of room (e.g. office, bedroom, living room, etc.) in which the source instance of system 20 was installed, the cardinal compass orientation (e.g. north, south, east, west) of the window on which the source instance of system 20 was installed, the climate zone in which the source instance of system 20 was installed, the type of shading device (e.g. shade, blind, smart window, etc) incorporated in the source instance of system 20, etc.

Determining the variance of values of s, for each adjust_shading(s) command associated with a particular value of j, across all the source systems installed in a particular type of room. This variance could then be used to decide between use of an adjust_shading(s) or don't_adjust default for that value of j: for example, a large variance would suggest the use of a don't_adjust default, while a small variance would suggest the use of an adjust_shading(s) default.

If empirically derived defaults are used, then step 30 would consist simply of the operations necessary to transfer those empirically derived default commands into set {command(j):}.

Shading-Device-Specific Defaults

In the preferred embodiment, the value of s in each adjust_shading(s) command represents the desired relative shading (0% to 100%) to be provided by shading device 21. In establishing the adjust_shading(s) default commands, it may be advantageous to consider the unique characteristics of various types of shading device.

Many types of adjustable shading device are known in the art, including:

Smart windows capable of more or less continuous control of the admitted light. These include windows based on Electro-Chromic (EC) and Suspended-Particle Device (SPD) technologies.

Liquid Crystal (LC) smart windows capable of discrete control of the view (by changing between transparent and translucent states), without substantially affecting the amount of admitted daylight.

Variable-aperture window coverings, such as cellular shades, roller shades, and drapes. These provide adjustable shading by varying the exposed area of the host window.

Venetian blinds, both horizontal and vertical, in which shading is provided by an array of parallel oblong slats. Such blinds can be operated in either a variable-aperture mode or in a tilting mode. In the variable aperture mode, the slats can be raised or lowered (in the case of a horizontal blind) or traversed (in the case of a vertical blind) to vary the exposed area of the window. In the tilting mode, each slat can be rotated about its long axis to provide more or less continuous control of the admitted daylight—or to block light from certain directions while admitting light from other directions.

Because of these unique characteristics, a user's preferred relative shading setting—and hence, the appropriate value of s for an adjust_shading(s) default command—in a given environmental state may depend on the specific type of shading device incorporated in system 20.

Consider, for example, environmental states in which direct sun is incident on the window. If a variable-aperture window covering (such as a cellular shade) is used, a user might prefer a relative shading setting of 100% in such states, because such a window covering may have to be fully closed to block glare associated with direct sun. If, however, a continuously controllable smart window is used (such as an SPD-based smart window), then the same user might prefer a low but non-zero relative shading setting (e.g. 95% shading), to control glare while still admitting useful natural illumination. Similarly, if a Venetian blind is used, the same user might prefer a relative shading setting that causes the slats to be tilted just enough (depending on the sun's angular position relative the host window) to block direct sun while still admitting useful natural illumination.

Thus, it may be advantageous to consider the unique characteristics of the selected shading device in establishing default values of set {command(j):} of automated shading commands. For example, different algorithms or rules could be established for each type of shading device to predict the appropriate value of s for each value of j. More preferably, empirical data on users' shading preferences could be binned according to the type of shading device, allowing separate sets of default {command(j):} values to be generated for each type of shading device.

Use of Absolute Vice Relative Shading Settings

As previously described, each automated shading command within set {command(j):} can be either an adjust_shading(s) or a don't_adjust command. In the preferred embodiment, argument s of each adjust_shading(s) command represents a relative shading setting, but s could alternatively represent an absolute shading setting (i.e. a value of setting).

Relative Settings

In the preferred embodiment, the value of s in each adjust_shading(s) command represents a desired relative setting (0% to 100% shading) of shade 61 of window covering 21A. This relative setting must be translated into an absolute setting (i.e. a value of variable setting, which tracks the displacement of motor 63) before an adjust_shading(s) command can be executed. Similarly, after execution of every deliberate shading command, the value of setting must be translated into a value of s before the appropriate adjust_shading(s) command can be updated. However, while these translation steps cost memory and processing cycles, the use of relative settings offers significant advantages:

- Relative shading settings can be defined before the minimum and maximum values of setting are known. This allows step 30 of FIG. 14, in which each member of set {command(j):} is initialized to default values, to be performed before step 71.
- This, in turn, means that step 30 could be performed at the factory, eliminating the need to encode the associated software operations in the final software or firmware executed by microcontroller 24A and thereby reducing the memory requirements.
- Further, because relative settings can be defined without regard to the minimum and maximum values of setting, they are applicable to many types of shading device—including pleated shades, curtains, or smart windows—regardless of size or design. This means that step 30 could typically be performed before the specific make, model, or type of shading device 21 is known.
- For the same reason, the use of relative settings allows set {command(j):} to be shared between different instances of system 20. In particular, the values of set {command(j):} for a fully taught instance of system 20 could be used as default values for another instance of system 20, greatly shortening the teaching interval.

Use of Absolute Settings

However, as previously noted, the use of relative shading settings requires translation of each relative setting into an absolute setting prior to execution of each automated shading command, and translation of each absolute setting into a relative setting after execution of each deliberate shading command (i.e. to update the corresponding automated shading command). If it is desired to eliminate these translation steps, and if the aforementioned advantages of relative shading settings are not important in a given application, then the preferred embodiment could be readily adapted to use absolute settings instead of relative settings. This would entail three modifications:

- Variable s would be re-defined to refer to an absolute setting of shade 61 (i.e. a particular value of setting), rather than a relative shading setting. Thus, for example, instead of the degree of relative shading, s could refer to the value of a motor position counter in a motorized window covering, or the value of the drive voltage applied to a Smart Window based on Suspended Particle Device (SPD) technology.
- If it is desired to initialize some members of set {command (j):} to adjust_shading(s) commands (as in the preferred embodiment), then initialization steps 70 of FIG. 14 would be re-ordered so that step 30 occurs after step 71. This is necessary because the range of setting—and, hence, of s—will not be known until the travel limits of shade 61 are established in step 71.
- If, however, all members of set {command(j):} are initialized to don't_adjust commands, then initialization step 30 could be performed at any time prior to usage of system 20.
- The operations to map s into a value of setting in step 31, and to map setting into a value of s in step 32, would no longer be necessary—because s and setting would both refer to an absolute setting of shade 61—and would be eliminated.

Special Considerations Related to Use of Venetian Blinds

In the preferred embodiment, shading device 21 is motorized window covering 21A, which incorporates shade 61. However, in many applications, it will be advantageous to substitute a conventional horizontal Venetian blind for shade 61.

A horizontal blind consists of an array of horizontal slats suspended by lift cords. Such a blind offers two degrees of adjustment: the slats can be lifted, or the slats can be tilted along their long axis. As is known in the art, either or both the lift and tilt functions can be motorized.

Motorization of Lift Function

If only the lift function is motorized, then there are no special considerations regarding substitution of a horizontal Venetian blind for shade 61.

Motorization of Tilt Function

However, in most single-function motorized blinds, the tilt, rather than lift, function is motorized. This is because motorization of the tilt function can be done with a smaller motor, and because the tilt function provides finer control of the admitted daylight.

Use of a tilt-only motorized blind imposes special considerations in implementing my invention, because—unlike a motorized shade—the degree of shading provided by a blind does not vary monotonically with the tilt of the slats. Instead, the shading is maximized when the slats are at either tilt limit, and minimized when the slats are horizontal. Further, the solar-optical properties of a blind differ significantly at the two tilt limits. For example, a blind in which the inward-facing edges of the slats are tilted fully upward will be more effective at blocking direct sun than a blind in which the inward edges of the slats are tilted fully downward.

Therefore, substitution of a tilt-only motorized blind for motorized window covering 21A would necessitate certain modifications to the preferred embodiment.

Revised Definition of Signals Produced by User Interface 23

In the preferred embodiment, signaling means 42 and 43 issue "increase shading" and "decrease shading" signals, respectively, which cause motor 63 to be operated in different directions. However, in a motorized blind, the shading can either increase or decrease, depending on the slat tilt angle, in both directions of motor operation. Therefore, if a motorized blind is substituted for motorized window covering 21A, then the signals issued by means 42 and 43 should be re-designated "tilt down" and "tilt up", respectively.

Similarly, the definition of the signals produced by signaling means 44 and 45 should be revised. In the preferred embodiment, signaling means 44 and 45 issue "Set Open/Lights On" and "Set Closed/Lights Off" signals, respectively. However, if a motorized blind is substituted for motorized window covering 21A, then the signals issued by means 44 and 45 should be designated "Down Limit/Lights On" and "Up Limit/Lights Off" respectively. Then, during step 71 to establish the shading limits, the user would actuate means 44 to issue the "Down Limit" signal after the slats have been tilted so that the inward-facing edges are fully downward. Similarly, the user would actuate means 45 to issue the "Up Limit" signal after the slats have been tilted so that their inward-facing edges are fully upward.

These modifications would have no impact on the implementation of system 20, other than the identification and labeling of the signaling means and the operating instructions for the user.

Modifications Related to Use of Adjust_Shading(s) Default Commands

In the preferred embodiment, some members of set {command(j):} are initialized to adjust_shading(s) default commands. The value of s for each adjust_shading(s) default command represents a prediction of the user's preferred relative shading setting (0% to 100%) in the corresponding value of state. Before each adjust_shading(s) command is executed, the value of s is mapped, via linear interpolation, to a desired value of setting. Similarly, following execution of each deliberate shading command, the new value of setting is mapped, via linear interpolation, to a value of s before the corresponding command(j) is updated. However, if a tilt-only motorized blind is substituted for motorized window covering 21A, then one of the following modifications should be made to the aforementioned processes:

Use of an alternative interpretation of variable s when establishing default adjust_shading(s) commands.

Use of different mapping functions to map values of s to values of setting, and vice-versa.

Omission of default adjust_shading(s) commands, in favor of initializing every member of set {command(j):} to don't_adjust default commands.

Alternative Interpretation of Variable s

If a tilt-only blind is used instead of a shade, then s should be interpreted as representing the approximate relative tilt angle of the slats, rather than the relative shading setting, in establishing values of s for adjust_shading(s) default commands. This will yield different values of s for certain conditions.

For example, suppose that s=0% represents the "inward facing slat edges downward" tilt limit, s=50% represents horizontal slat tilt, and s=100% represents the "inward facing slat edges upward" tilt limit. Then, minimum shading with a blind would call for s=50% (versus s=0% for a shade), because a blind's relative shading is minimized when the slats are horizontal. With a blind, maximum shading to block direct sun would call for s=100% (as with a shade), because blinds are most effective at blocking sun when the slats are tilted so that their inward facing edges are fully upward. However, a blind can also block the view (e.g. to maintain privacy) while still admitting useful daylight; this might call for s=10%, because blinds typically admit a significant amount of light when the slats are tilted so their inward facing edges are nearly fully downward.

The only disadvantage in using such an alternative definition of s in establishing the default adjust_shading(s) commands is that such defaults could not be directly shared (without modification) with instances of system 20 using other types of shading device.

Alternative Mapping Functions

In the preferred embodiment, a linear mapping function is used to translate the value of s into a value of setting prior to execution of each adjust_shading(s) command, and the inverse mapping function is used to translate the value of setting into a value of s after execution of each deliberate shading command. The linear function maps the entire range of s (0% to 100%) into the entire range of setting (as established during initialization step 71).

If, however, a tilt-only motorized blind is substituted for motorized window covering 21A, and if s continues to be defined as the relative shading setting (rather than being redefined as the relative tilt angle, as discussed above), then an alternative function should be used to map s to setting, because the relative shading provided by the blind will not vary monotonically over the entire range of setting.

For example, the entire range of s (0% to 100%) could be mapped to just half the range of setting. This is a viable option because, under most conditions, the relative shading provided by a blind decreases monotonically as the slats are tilted in either direction away from horizontal. For example, a mapping function could be used which produces values of settings that cause the slats to tilt only between horizontal and the "inward-facing slat edges upward" limit. A disadvantage of this particular mapping function would be that it exploits only half of the blind's tilt-adjustment range. However, this may be acceptable in some applications.

Exclusive Use of Don't_Adjust Defaults

The aforementioned issues associated with the use of adjust_shading(s) default commands with a horizontal Venetian blind can be avoided if no such default commands are used, i.e. if each member of set {command(j):} is initialized to the don't_adjust default command. This would eliminate the need to establish a value of s for each of the user's anticipated shading preferences in each environmental state. In this case, the software implementation could be further simplified by using absolute shading settings, vice relative shading settings, as discussed elsewhere herein.

The disadvantage of this approach is that, as previously discussed, the teaching interval would be longer—and the short-term inconvenience greater—than if appropriate adjust_shading(s) defaults were included in set {command (j):}. However, as previously shown in FIG. 9, the resulting instance of system 20 would still achieve the same reduction the long-term inconvenience associated with deliberate shading adjustments. Further, the short-term inconvenience, while greater than that of the preferred embodiment, would be no greater than the reference level. Thus, such an instance of system 20 would offer the same qualitative advantages as the preferred embodiment over the prior art in reducing both the long-term and short-term inconvenience associated with deliberate shading adjustments.

Motorization of Both Lift and Tilt Functions

Motorized blinds are known in the art in which both the tilt and lift functions are motorized and independently controllable. The preferred embodiment of my invention could be easily modified to fully exploit the capabilities of such dual-function blinds.

Functionally, such a system could be considered as two instance of system 20—one employing a lift-only motorized blind and one employing a tilt-only motorized blind. Therefore, the information provided in the preceding paragraphs regarding the use of lift-only and tilt-only blinds should be sufficient to enable skilled practitioners to use my invention with dual-function blinds.

Of course, skilled practitioners will recognize that, to minimize cost, it will generally be advantageous to share some common elements—e.g. sensing means 22, control element 24, and some aspects of user input interface 23, among others—between the tilt and lift functions. On the other hand, some elements will be unique to each of the tilt and lift functions. For example, each function may have a separate instance of displacement sensor 64. Further, there would be a unique set {command(j):} of automated shading commands for each function, and unique default values would be used for each set.

The choice between unique and common components can be made according to conventional practice and the information provided herein, to suit the requirements of the application at hand.

Alternative Forms of Deliberate Shading Command

In the preferred embodiment, deliberate shading commands are asserted via "increase shading" and "decrease shading" signals produced by user input interface 23. Thus, the user performs a deliberate shading adjustment by actuating the appropriate signaling means within user input interface 23 until the desired relative shading setting is reached.

However, "random access" automated systems are known in which a desired setting can be directly commanded, and system 20 could be readily adapted to accept deliberate shading commands in such a form. For example, user input interface 23 could be modified to allow the user to specify a particular value of variable s, and to provide a signal encoding that value of s to control element 24. For example, user input interface 23 could be provided with a digital keypad and display for this purpose.

Alternatively, dedicated signaling means could be provided within user input interface 23 to command specific, predetermined values of s, such as 0% and 100%. For example, "fully open" and "fully close" signaling means (e.g. via momentary contact switches actuated by pushbuttons) could be provided for this purpose.

The use of such direct commands may provide added convenience in some applications, at the expense of increased complexity of user input interface 23.

The specific format of deliberate shading commands is incidental to my invention, and can be established in accordance with the information provided herein and conventional practice to suit the specific requirements of the application at hand.

Alternative Procedures for Updating of Automated Shading Commands

In the preferred embodiment, each automated shading command command(j), which is initialized to either a don't_adjust or an adjust_shading(s) command, is automatically updated to an adjust_shading(s) command after each deliberate shading adjustment in state j. This automatic updating is the mechanism by which system 20 "learns" the user's shading preferences.

However, other procedures for updating automated shading commands may be advantageous in some applications, including (but not limited to) the following:

Making the updating contingent upon issuance of a user command, rather than automatic.

Allowing the user to make deliberate shading adjustments without automatic updating when desired.

Locking out, or preventing, updating of default automated shading commands in selected environmental states.

These alternative procedures are described in the following paragraphs.

Deliberate Versus Automatic Updating

In the preferred embodiment, each deliberate shading adjustment automatically updates the automated shading command associated with the prevailing environmental state. However, some deliberate shading adjustments may be "one time only" or occasional adjustments that do not reflect the user's long-term shading preferences.

Thus, in some applications, it may be advantageous to update the prevailing automated shading command only upon receipt of a user command to do so. This could be done, for example, via the following modifications to the preferred embodiment:

Adding a "learn" signaling means (e.g. a dedicated "learn" pushbutton) to user input interface 23.

Modifying operating step 32 to remove the operations associated with updating of the prevailing command(j).

Adding a new operating step to update the prevailing command(j) only upon receipt of the "learn" signal, wherein such updating consists of changing the prevailing command(j) to an adjust_shading(s) command in which s reflects the value of the prevailing shading setting.

Users would actuate the "learn" signaling means only after deliberate shading adjustments that reflect long-term shading preferences, and not after occasional or "one-time" shading adjustments.

User-Enabled Automatic Updating Mode

As an alternative to the above modification, additional commands could be defined that enable and disable automatic updating of the prevailing automated shading commands. This could be done, for example, via the following modifications to the preferred embodiment:

Adding "automatic learning on" and "automatic learning off" signaling means to user input interface 23.

Adding an operating step to register the most recent actuation of the "automatic learning on" and "automatic learning off" signaling means.

Modifying operating step 32 to inhibit the operations associated with updating of the prevailing command(j) if the "automatic learning off" signaling means was actuated more recently than the "automatic learning on" signaling means.

Deliberate Shading Commands without Automatic Updating

As an alternative to the aforementioned modifications, additional, special, deliberate shading commands could be defined that cause deliberate shading adjustments without automatic updating of the prevailing automated shading commands. This could be done, for example, via the following modifications to the preferred embodiment:

Adding "increase shading without learning" and "decrease shading without learning" signaling means to user input interface 23.

Modifying operating step 32 to respond to the "increase shading without learning" and "decrease shading without learning" signals, so that:

The shading is increased or decreased in accordance with the signal, but

The operations associated with updating of the prevailing command(j) are not performed.

Users would then actuate original "increase shading" and "decrease shading" signaling means 42 and 43 to make deliberate shading adjustments that reflect long-term shading preferences, and the "increase shading without learning" and "decrease shading without learning" signaling means to make occasional or one-time-only deliberate shading adjustments.

Locking-Out of Updating in Selected Environmental States

In some applications, it may be advantageous to lock out, or prevent, updating of the default automated shading commands in certain environmental states. This may be the case, for example, when default commands are selected for reasons other than expected occupant preferences.

Locking-Out of Updates to Adjust_Shading(s) Commands

For example, in a system used in a non-residential building, default values of certain members of {command(j):} may be selected to minimize solar heating loads on the building. In this case, it may be advantageous to allow deliberate shading adjustments—but to prevent automatic update of the prevailing automated shading commands—in environmental states in which solar heating is expected. This could be done, for example, via the following modifications to the preferred embodiment:

Defining a new automated shading command, adjust_without_update(s), that can be assigned to any command(j). Like the adjust_shading(s) command, the adjust_without_update(s) command would cause an automatic shading adjustment to a relative shading setting of s when state changes to j. However, unlike the adjust_shading(s) command, the adjust_without_update(s) command would inhibit updating of the value of s after deliberate shading adjustments in state j.

Initializing selected members of set {command(j):} to the adjust_without_update(s) command. In this example, an adjust_without_update(100%) default would be assigned for each value of j for which substantial solar heating loads are expected.

Modifying step 32 to inhibit automated updating of the prevailing automated shading command if the prevailing command is an adjust_without_update(s) command.

Thus, automatic updating of the default automated shading commands would be disabled in the elected states, although users would still be able to make deliberate shading adjustments in those states.

Locking-Out of Updates to Don't_Adjust Commands

In the preferred embodiment, a don't_adjust command is automatically updated to an adjust_shading(s) command after any deliberate shading adjustment in the corresponding environmental state. In some applications, however, it may be advantageous to retain the don't_adjust command indefinitely in some environmental states—specifically those states in which a deliberate shading adjustment cannot be confidently expected to represent the users' long-term shading preference. This situation can arise when a room is shared between occupants who might have conflicting shading preferences in certain states, or when a given user's shading preference in a given state depends partly on information not captured in the value of state.

Such situations could be accommodated via the following modifications to the preferred embodiment:

Defining a new automated shading command, don't_adjust_or_update, that can be assigned to any command(j). Like the don't_adjust command, the don't_adjust_or_update command would not cause any automatic shading adjustment when state changes to j. However, unlike the don't_adjust command, the don't_adjust_or_update command would not be updated to an adjust_shading(s) command after a deliberate shading adjustments in state j.

Initializing selected members of set {command(j):} to the don't_adjust_or_update command. In this example, this would be done for each value of j in which conflicting shading preferences might be expected.

Modifying step 32 to inhibit automated updating of the prevailing automated shading command if the prevailing command is a don't_adjust_or_update command.

Thus, no automated shading adjustment would occur upon transition into the selected states, although users would still be able to make deliberate shading adjustments in those states.

Additional Capabilities

Practitioners in the art will appreciate that system 20 can be readily adapted to provide additional capabilities, some of which are discussed in the following paragraphs.

Suspend/Resume Mode

For example, additional signaling means could be added to enable the user to suspend and resume the automatic shading capability when desired (e.g. by suspending operating steps 80). This could be done, for example, via the following modifications to the preferred embodiment:

Adding "suspend" and "resume" signaling means to user input interface 23.

Adding an operating step to register the most recent actuation of the "suspend" and "resume" signaling means.

Modifying operating step 31 to inhibit the operations associated with executing the prevailing automated shading command command(j) if the "suspend" signaling means was actuated more recently than the "resume" signaling means.

Daylighting Mode

The preferred embodiment of my invention performs automated shading adjustments only upon a change in the variable state. However, it may be desirable in some applications to provide the capability for automated shading adjustments without a change in state.

Such an application is daylighting—an energy saving technique that uses daylight to reduce the need for artificial illumination. As is known in the art, the energy savings available through daylighting can be substantially increased through use of a dynamic daylight control system, i.e. an automated shading system that dynamically regulates the daylight admitted into a building. I disclose such a system, for example, in my U.S. Pat. No. 6,084,231 (2000).

System 20 could be adapted to provide the same dynamic-daylight control functionality as the system disclosed in my U.S. Pat. No. 6,084,231, while retaining all the advantages of the instant invention. This could be done, for example, via the following modifications to the preferred embodiment:

Substituting motorized window covering 21A with an electronically controlled shading device better suited to provide continuous control of the admitted daylight, e.g. a motorized horizontal Venetian blind or a Smart Window.

Adding interior daylight sensing means to sense the daylight admitted by the window. I disclose such means, for example, in my aforementioned patent 6,084,231.

Defining a new type of automated shading command. The preferred embodiment, as described previously, includes two types of automated shading command: a don't_adjust command, and an adjust_shading(s) command. In order to implement dynamic daylight-control capability, a daylighting(d) command could be defined that causes the system to perform dynamic daylighting control, as described in my aforementioned patent 6,084,231. The argument d of this command would represent the desired admitted daylight level as sensed by the interior daylight sensing means (rather than the relative shading setting, as in variable s of the adjust_shading(s) command). The appropriate members of set {command(j):} could then be set to the daylighting(d) command during initialization (for example, it may be desirable to enable dynamic daylight control only during daytime when the room lights are on). Each deliberate shading adjustment while a daylighting(d) command is operative would cause the argument d to be updated to equal the new sensed daylight level, in the same way that the relative shading setting s of the preferred embodiment is updated after each deliberate shading adjustment. Thus, the system would be capable of learning not just the user's preferred fixed shading settings for various states, but also the user's preferred daylight level for those states in which daylighting is underway.

With these modifications, system 20 would offer the advantages of both sensor-based discrete control and sensor-based continuous control systems.

Provision to Restore Defaults

In the preferred embodiment, each member of set {command(j):} of automated shading commands is initialized to a default value in step 30. Subsequently, the default value associated with a particular value of j is updated after execution of a deliberate shading command in the corresponding state.

If desired, system 20 could be given the capability to restore {command(j):} to the default values upon user command. This could be done, for example, via the following modifications to the preferred embodiment:

- Adding "restore defaults" signaling means to user input interface 23.
- Providing storage means to store the original set of default values.
- Adding operating steps to cause the current values of set {command(j):} to be replaced with the stored default values upon assertion of the "restore defaults" signal.

Alternatively, the operating steps of the preferred embodiment could be modified, in a conventional manner, so that the defaults are automatically restored after a deliberate or power-on reset of microcontroller 24A.

Provision to Select Between Alternative Sets of Defaults

As previously noted, step 30 involves initializing set {command(j):} of automated shading commands to default values, with adjust_shading(s) defaults used for those values of j for which the user's shading preferences can be confidently anticipated. As previously discussed, this can shorten the teaching interval, as well as increase the initial effectiveness of system 20.

However, the user's anticipated shading preferences will obviously depend on factors that may not be predictable before step 30 is performed. For example, the anticipated shading preferences may depend on the type of room in which system 20 will be installed—e.g. office, bedroom, living room, solarium, etc. Thus, it may be advantageous to include provisions to store several sets of default values, with the operative set selected by the user when step 30 is executed. This could be done, for example, via the following modifications to the preferred embodiment:

- Modifying user input interface 23 to include signaling means to generate a "default selection" signal to select a set of defaults from two or more alternative sets of defaults.
- Providing additional memory to store the desired number of sets of default automated shading commands.
- Modifying step 30 to cause the selected set of defaults, based on the "default selection" signal, to be transferred into set {command(j):}.

Capability to Download and Upload Defaults

After system 20 becomes fully taught, set {command(j):} contains the user's shading preferences for each state. This information may be advantageously used to empirically establish default automated shading commands for other instances of system 20. As will be evident to practitioners in the art, system 20 could easily be modified to allow this information to be downloaded (or transferred) to another device, such as a computer or another instance of system 20. Similarly, it may be advantageous to provide system 20 with the capability to upload (or accept) default automated shading commands from another device, such as a computer or another instance of system 20. Such capabilities could be provided, for example, via the following modifications to the preferred embodiment:

- Adding a suitable conventional data interface, either wired or wireless (e.g. via ZigBee, Bluetooth, IRDA, Ethernet, WiFi, etc.).
- Adding appropriate operating steps to cause the values of set {command(j):} to be shared (i.e. downloaded or uploaded) across the interface at appropriate times.

Use of Multiple Shading Devices

As will be evident to practitioners in the art, system 20 could be modified to include multiple shading devices (or to control multiple shading functions provided by a single shading device). There are at least three situations in which such an embodiment would be advantageous:

- Situations in which several windows are located in sufficient proximity that they share substantially the same environmental state, as defined by variable state.
- Use of multiple shading devices on a single window, e.g. use of motorized sheer curtains and motorized blackout (e.g. opaque) curtains on the same window.
- Use of a shading device that provides more than one independently controllable shading function, such a dual-function motorized blind with motorized lift and tilt capability.

The preferred embodiment could be modified to include multiple shading devices or control multiple shading functions, for example, via the following modifications:

- Modifying user interface 23 so that it is capable of generating "increase shading", "decrease shading"' "opened", and "closed" signals for each shading device or function.
- Providing a separate set {command(j):} of automated shading commands for each shading device or function.
- Modifying the method of operation so that initialization steps 70 and operating steps 80 are executed independently for each shading device, except for those operations associated with evaluating the values of condition and state (which would be performed for all the shading devices or functions).

This would allow each shading device or function to be operated independently, while still providing significant economies by sharing much of the hardware (especially sensing means 22, control element 24, and elements of user interface 23) among the various shading devices or functions.

Applications Other than Automated Shading

While my invention is directed toward automated shading systems, it can also be applied to any automated system that has the object of automatically adjusting one, or more, variables as a function of changing conditions, in anticipation of a user's preferences. In addition to shading settings, such variables include, for example, temperature, sound volume, lamp brightness, humidity, etc.

For example, my invention could be applied to automated thermostats. Indeed, a useful embodiment of an automated thermostat could be obtained simply by replacing electronically controlled shading device 21 of FIG. 6 with an electronically controlled HVAC (Heating, Ventilation, and Air Conditioning) system.

CONCLUSIONS, RAMIFICATIONS, AND SCOPE

As this disclosure makes clear, my innovative system for, and method of, automated window shading adjustment is more effective that the prior art in reducing the frequency of required deliberate shading adjustments, while eliminating the need for an inconvenient teaching process. Thus, my invention substantially eliminates both the short-term and long-term inconvenience associated with window shading adjustments. Yet, it can be implemented using simple and inexpensive hardware. Further, although automated shading system 20 is the preferred embodiment of my invention, many other useful embodiments are possible.

Those skilled in the art will recognize that the construction and function of the elements composing the preferred and alternative embodiments described herein may be modified, eliminated, or augmented to realize many other useful embodiments, without departing from the scope and spirit of the invention as recited in the appended claims.

I claim:

1. A method of automatically adjusting a window shading device, said method comprising the following steps:
 a. characterizing an environmental condition via a discrete condition variable; said discrete condition variable being a function of at least two environmental characteristics;
 b. characterizing an environmental state via a discrete state variable, said discrete state variable being a function of N most recent values of said discrete condition variable, N being at least 2, said discrete state variable thereby representing a history of values of said discrete condition variable; and
 c. adjusting said window shading device upon a change in value of said discrete state variable.

2. A method of automatically adjusting a window shading device of a shading system, said shading system capable of user-initiated deliberate shading adjustments in addition to automatic shading adjustments, said method comprising the following steps:
 a. characterizing an environmental state via a discrete state variable, said discrete state variable being a function of at least two environmental characteristics;
 b. initializing a first automated shading command to a do-not-adjust-command, said first automated shading command corresponding to a first value of said discrete state variable;
 c. changing said first automated shading command from said do-not-adjust command to a first adjust shading command upon a deliberate shading adjustment of said window shading device to a first setting when said discrete state variable has said first value; and
 d. adjusting said window shading device to said first setting upon a change of value of said discrete state variable to said first value, if and only if said first automated shading command is said first adjust shading command.

3. The method of claim 2, further comprising the following steps:
 a. initializing a second automated shading command to a second adjust shading command, said second automated shading command corresponding to a second value of said discrete state variable, said second adjust shading command specifying a second setting of said window shading device; and
 b. adjusting said window shading device to said second setting upon a change of value of said discrete state variable to said second value.

4. The method of claim 2, further comprising the following steps:
 a. initializing a third automated shading command to a daylighting command, said third automated shading command corresponding to a third value of said discrete state variable; and
 b. adjusting said window shading device to dynamically regulate admitted daylight when said discrete state variable has said third value.

5. A method of automatically adjusting a window shading device of a shading system, said shading system capable of user-initiated deliberate shading adjustments in addition to automatic shading adjustments, said method comprising the following steps:
 a. characterizing an environmental state via a discrete state variable, said discrete state variable being a function of at least two environmental characteristics;
 b. initializing a first automated shading command to a do-not-adjust-command, said first automated shading command corresponding to a first value of said discrete state variable;
 c. initializing a second automated shading command to an adjust shading command, said second automated shading command corresponding to a second value of said discrete state variable;
 d. adjusting said window shading device upon a change of value of said discrete state variable to a new value, said new value corresponding to a new automated shading command, if and only if said new automated shading command is an adjust shading command.

6. The method of claim 5, further comprising the following steps:
 a. initializing a third automated shading command to a daylighting command, said third automated shading command corresponding to a third value of said discrete state variable; and
 b. adjusting said window shading device to dynamically regulate admitted daylight when said discrete state variable has said third value.

* * * * *